(12) United States Patent
Noe et al.

(10) Patent No.: US 9,968,686 B2
(45) Date of Patent: May 15, 2018

(54) ANTISENSE OLIGONUCLEOTIDES WITH IMPROVED PHARMACOKINETIC PROPERTIES

(71) Applicant: University of Vienna, Vienna (AT)

(72) Inventors: Christian R. Noe, Vienna (AT); Mehrdad Dirin, Vienna (AT); Johannes Winkler, Vienna (AT); Bodo Lachmann, Vienna (AT); Ernst Urban, Vienna (AT)

(73) Assignee: UNIVERSITY OF VIENNA, Vienna (AT)

( * ) Notice: Subject to any disclaimer, the term of this patent is extended or adjusted under 35 U.S.C. 154(b) by 0 days. days.

(21) Appl. No.: 14/911,264

(22) PCT Filed: Sep. 9, 2014

(86) PCT No.: PCT/EP2014/069174
§ 371 (c)(1),
(2) Date: Feb. 9, 2016

(87) PCT Pub. No.: WO2015/032968
PCT Pub. Date: Mar. 12, 2015

(65) Prior Publication Data
US 2016/0193354 A1    Jul. 7, 2016

(30) Foreign Application Priority Data

Sep. 9, 2013   (EP) .................................... 13183561

(51) Int. Cl.
| | | |
|---|---|---|
| *C07H 21/04* | (2006.01) |
| *A61K 47/48* | (2006.01) |
| *A61K 31/7088* | (2006.01) |
| *A61K 33/24* | (2006.01) |
| *A61K 45/06* | (2006.01) |
| *A61K 31/713* | (2006.01) |
| *C12N 15/113* | (2010.01) |

(52) U.S. Cl.
CPC .... *A61K 47/48315* (2013.01); *A61K 31/7088* (2013.01); *A61K 31/713* (2013.01); *A61K 33/24* (2013.01); *A61K 45/06* (2013.01); *A61K 47/48215* (2013.01); *C12N 15/113* (2013.01); *C12N 2310/11* (2013.01); *C12N 2310/14* (2013.01); *C12N 2310/351* (2013.01); *C12N 2320/30* (2013.01)

(58) Field of Classification Search
USPC ....................................................... 536/24.5
See application file for complete search history.

(56) References Cited

U.S. PATENT DOCUMENTS 6,153,737 A    11/2000   Manoharan et al.

| | | | |
|---|---|---|---|
| 2006/0058266 A1* | 3/2006 | Manoharan ...... | A61K 47/48023 514/81 |
| 2010/0190691 A1 | 7/2010 | Epenetos et al. | |

OTHER PUBLICATIONS

Shengxi Jin et al., Synthesis of Amine- and Thiol-Modified Nucleoside Phosphoramidites for Site-Specific Introduction of Biophysical Probes into RNA, The Journal of Organic Chemistry, vol. 70, No. 11, pp. 4284-4299 (2005).
Johannes Winkler et al., Oligonucleotides Conjugated to Short Lysine Chains, Bioconjugate Chemistry, vol. 16, No. 4, pp. 1038-1044 (2005).
S. B. Rajur et al., Covalent Protein-Oligonucleotide Conjugates for Efficient Delivery of Antisense Molecules, Bioconjugate Chemistry, vol. 8, No. 6, pp. 935-940 (1997).
Soo Hyeon Lee et al., Di- and Triblock siRNA-PEG Copolymers: PEG Density Effect of Polyelectrolyte Complexes on Cellular Uptake and Gene Silencing Efficiency, Macromolecular Bioscience, vol. 11, No. 3, pp. 410-418 (2010).
C. W. Gundlach et al., Synthesis of Guanosine Analogs Bearing Pendant Alkylthiol Tethers, Tetrahedron Letters, vol. 38, No. 23, pp. 4039-4042 (1997).
Jay T. Goodwin et al., Design, Synthesis, and Analysis of Yeast tRNA Phe Analogs Possessing Intra- and Interhelical Disulfide Cross-Links, J. Am. Chem. Soc., vol. 118, pp. 5207-5215 (1996).
Written Opinion of the International Preliminary Examining Authority for International Application PCT/EP2014/069174 dated Aug. 6, 2015.

(Continued)

*Primary Examiner* — Kimberly Chong
(74) *Attorney, Agent, or Firm* — Nevrivy Patent Law Group P.L.L.C.

(57) ABSTRACT

The invention relates to an antisense or siRNA oligonucleotide or conjugate with improved pharmacokinetic properties, methods of producing the same as well as the use of such compounds and conjugates, e.g. as pharmaceutical composition, a pharmaceutical kit, a medicament or a tool in biomedical research.
The conjugates of the invention have the formula I being P-(L-S—S—Y—X)$_n$, wherein P represents a natural, artificial and/or modified oligonucleotide, L represents a linker group attached to one or more nucleosides at any position within the oligonucleotides sequence; S represents sulfur; X represents a ligand; Y represents a spacer and n is an integer ranging from 1 to the oligonucleotide length of P.
The oligonucleotides of the invention have the formula II being P-(L-S—R)$_n$, wherein P represents a natural, artificial and/or modified oligonucleotide, L represents a linker group attached to one or more nucleosides at any position within the oligonucleotides sequence, S represents sulfur, R represents either hydrogen or a thiol protecting group, preferably trityl or tertiary butyl, and n is an integer ranging from 1 to the oligonucleotide length of P.
In addition, the pharmaceutical composition or pharmaceutical kit or conjugate can be used for the treatment of a disease or disorder that can be at least in part alleviated by therapy, wherein the disease or disorder is selected from the group consisting of bacterial infections, viral infections, cancer, metabolic diseases and immunological disorders and preferably cancer.

15 Claims, 17 Drawing Sheets

(56) References Cited

OTHER PUBLICATIONS

Written Opinion of the International Searching Authority for International Application PCT/EP2014/069174 dated Mar. 12, 2015.
European Search Report and Annex to the European Search Report for corresponding application EP 13183561 dated Jan. 20, 2014.
International Search Report for International Application PCT/EP2014/069174 dated Mar. 12, 2015.
International Preliminary Report on Patentability for International Application PCT/EP2014/069172 dated Nov. 24, 2015.

* cited by examiner

ANTISENSE OLIGONUCLEOTIDES WITH IMPROVED PHARMACOKINETIC PROPERTIES

REFERENCE TO A SEQUENCE LISTING SUBMITTED ELECTRONICALLY VIA EFS-WEB

The content of the sequence listing (Name: sequence-_listing_US.txt; Size: 546 bytes; and Date of Creation: Feb. 9, 2016) electronically submitted via EFS-Web is incorporated by reference in its entirety.

FIELD OF THE INVENTION

The present invention relates to antisense and siRNA oligonucleotides and conjugates having improved pharmacokinetic properties bearing a cleavable disulfide linker attached to the 2'-position of the nucleoside at at least the 3' end and to methods of producing such compounds as well as the use thereof.

BACKGROUND OF THE INVENTION

Antisense oligonucleotides (ASONs) are a promising new class of therapeutics designed to attenuate or correct the expression of discordantly expressed genes with high specificity and avidity. Efficiency of ASONs in cell culture is known for a long time. They have become nowadays an indispensable tool in biomedical research. Clinical proof of efficacy has been established with the approval of the first ASON therapeutic, fomivirsen sodium in 1998 (marketed as Vitravene™, Isis Pharmaceuticals).

At present, there are several clinical trials underway using antisense compounds directed at various targets playing mainly a role in cancer, viral diseases and inflammatory disorders either as single-agent or in combination with other related therapeutics. Yet, after more than three decades from the inception of antisense technology and in spite of numerous promising clinical trial reports, fomivirsen and mipomersen are the only antisense therapies on the market. Nevertheless, its route of administration, i.e. intravitreal injection, is indicative of its lack of appropriate pharmacokinetic properties. A major challenge in widespread use of ASONs is their yet inadequate uptake and biological stability for a sufficient length of time to achieve the desired effect. This has prompted the development of new generations of ASONs.

The first-generation modifications (first-generation ASONs) were primarily on the backbone of the ODN molecules, such as phosphorothioate oligodeoxynucleotides (PS-ODNs), methylphosphonates, and phosphoramidates. Like their native counterparts, PS-ODNs have a negatively charged backbone and are capable of supporting RNase H activity offering nuclease resistance sufficient for parenteral administration. At the same time, this simple chemical modification imparts favorable pharmacokinetic properties including improved tissue distribution, reduced urinary excretion, and prolonged residence time in tissues and cells. These intrinsic properties have made PS-ASONs the structure of choice as first-generation ASONs.

With respect to clinical application it can be stated that obviously the phosphorothioates "have made the race". However, their widespread clinical application may be limited as a result of their rather poor pharmacodynamic and safety issues. Although concern about such issues has been raised since a long time, it was only recently confirmed that the thioate modification as a structural moiety is sequence-independently associated with an intrinsic apoptotic effect. Based on these results, the use of the phosphorothioates seems to be acceptable only in therapeutic applications where an apoptotic effect is desired or at least acceptable.

The second-generation ASONs represent oligonucleotides in which the structural modification is not limited to the backbone linkage but includes structural modifications of the nucleoside. They were designed to improve the efficacy of the ASONs, to increase the binding affinity, to enhance the nuclease resistance, to improve cellular absorption and to modulate the protein binding of oligonucleotides. The 2'-modification was evidently the winner within this generation. In 1991, the superior biological efficacy was demonstrated of 2'-O-methyl and 2'-O-ethyl oligoribonucleotides compared with the unmodified antisense RNA for studying snRNP-mediated pre-mRNA splicing and processing.

The degree of nuclease resistance conferred by a simple 2'-O-methyl substituent however does not completely suffice for the corresponding phosphodiester-based oligonucleotides to be useful for antisense application. The use of mixed backbone oligonucleotides which contain appropriately placed segments of phosphorothioate oligodeoxynucleotides and differently modified oligodeoxynucleotide or oligoribonucleotides in the intervening gap have shown improvements over PS-ODNs.

More recently, minimally-modified antisense ODNs have been introduced. These are phosphodiester ODNs protected by two to five PS residues at their 3'-end by two PS residues at their 5'-end against potential degradation by 5'-exonucleases, and by phosphorothioate linkages at internal pyrimidine nucleotides against degradation by endonucleases. Definitely, all these thioate-containing modifications have to be assessed in the light of the intrinsic thioate toxicity mentioned above.

The third-generation ASONs represent major structural changes and contain a variety of modifications within the ribose ring and/or the phosphate backbone. Such modifications were frequently carried out in the frame of basic scientific research to promote the understanding of the mechanism of base pairing.

Undoubtedly, the goal of most of these modifications has been to improve the bio-stability and cellular uptake, to optimize tissue and cell distribution for a particular molecular target as well as being less toxic.

At this stage it has to be mentioned that during the early phases of antisense research the mechanism of inhibition was not fully delineated. Several "effector" approaches have been proposed, e.g. ribozymes, intercalators, etc. In this respect, the finding that the enzyme RNase H is cleaving the sense strand efficiently has made most of the other approaches obsolete and has focused the attention on the RNase H compatibility of specific modifications. It is not surprising however that most of these third-generation modifications (such as PMOs and LNAs) render them RNase H-incompetent.

In summary, there is no doubt about the pharmacodynamic potential of the antisense principle. Nevertheless, it is evident that during all phases of research it was rather the emergence of novel approaches in nucleic acid therapy, like siRNA or miRNA that has been driving the progress, while the equally important aspects of poor bioavailability and weak pharmacokinetic parameters have not yet received the required attention.

To date, the implicit aim has been to make enzyme-resistant DNA analogues capable of forming most stable hybrids with complementary DNA or RNA. Many of such analogues are now at hand, now it is time to focus more on biological parameters such as cellular uptake, bioavailability, and general pharmacokinetics. Appropriate balance of these properties enables drug molecules to attain and maintain sufficient systemic and/or target concentrations to exert therapeutic effects through optimum absorption, distribution, metabolism, and excretion (ADME) processes. Due to the awareness that the rather high attrition rate of compounds, observed only in the development phase, is caused by unfavorable ADME and toxicity properties, more and more efforts are being put to the field of ADME.

Natural oligonucleotides have a phosphodiester backbone that is susceptible to degradation by abundant nucleases present in vivo. Hence, oligonucleotides must be chemically modified or protected by appropriate formulations in order to be used as therapeutic agents.

With regard to the ADME properties of various classes of the ASONs, it seems that these agents share a common dilemma, i.e. poor pharmacokinetic properties, particularly poor bioavailability and cellular uptake. One of the approaches implemented to improve the antisense activity of nucleic acids is the development of suitable delivery systems. In cell culture studies, uptake-enhancing agents such as cationic lipids or polymers are routine tools to transfect the cells. However, in vivo co-administration of oligonucleotides with these agents has proved problematic owing to their unfavorable pharmacokinetics and considerable toxicity.

Another promising approach pursued to improve antisense activity relies on performing minor structural changes designed to alter multiple properties of the oligonucleotide, for instance, improving nuclease resistance, hybridization and cellular uptake of the oligonucleotide at the same time. Hence, a variety of chemical modifications have been designed including alterations in the backbone chemistry, modifications on the 2'-position of the ribofuranose ring, altered ring structure, conjugation with other molecules or oligomers, nucleobase modifications and others.

Rajur, S B et al. (Rajur, S B et al. Bioconjugate chemistry, 1997, 8(6), pp 935-940) describes a conjugate of an antisense oligonucleotide having a thiol linker to asiaglycoprotein via a disulfide bond.

In Lee, S H et al. (Lee, S H et al. Macromolecular Bioscience, 2010, 11(3), pp 410-418), a conjugate of a siRNA having a thiol linker to polyethylene glycol via a disulfide bond is described.

US 2010/190691 A1 describes a conjugate of siRNA having a thiol linker to cell penetrating peptides via a disulfide bond.

In U.S. Pat. No. 6,153,737 A a conjugate of a phosphorothioate oligonucleotide having a thiol linker at a 2' position to cholesterol via a disulfide bond is described.

Shengxi, J et al. (Shengxi, J et al. The Journal of organic chemistry, 2005, 70(11), pp 4284-4299) discloses nucleoside phosphoramidites for solid-phase synthesis with protected amine or thiol functional group. The nucleoside phosphoramidites either include each of the four common RNA nucleotides (U, C, A, and G) with a 2'-(2-aminethoxy)-2'-deoxy substitution or include each of the four common RNA nucleotides (U, C, A, and G) with an 2'-(2-mercaptoethoxy)-2'-deoxy substitution (i.e., a tethered 2'-thiol). Goodwin, J T et al. (Goodwin, J T et al. Journal of the American Chemical Society, 1996, 118(22), pp 5207-5215) discloses cross linked RNA, wherein the cross-linked RNA is achieved by two 2'-O-alkylthiol modified cytosine residues.

Gundlach, C W et al. (Gundlach, C W et al. Tetrahedron Letters, 1997, 38(23), pp 4039-4042) describes guanosine analogs exhibiting an alkylthiol substituent at the 2'-hydroxyl of the ribose.

SUMMARY OF THE INVENTION

Among the various modifications of oligonucleotides, now it was found that structural changes on the sugar moiety at the 2'-position of the ribose ring are particularly suited for minor modifications without compromising the hybridization affinity. One of the main strategies developed in the present invention is to improve the pharmacokinetics and pharmacodynamics of the antisense oligonucleotides by means of the "charge reversal" approach, i.e. through attachment of cationic peptides capable of crossing cellular membranes.

It was now surprisingly found that conjugates of oligonucleotides with peptides, in particular basic peptides or polyethylene glycol or oligoethylene glycol units, which are attached to the nucleotides of the oligonucleotide within the conjugate at a specific position via a cleavable disulfide linker provides for improved pharmacokinetic properties.

Surprisingly, it was now found that especially conjugates with improved pharmacokinetic properties were synthesized by coupling them at the 2'-position of the 3'-end to a ligand, e.g. L-lysine chains residues or polyethylene glycol chains through a cleavable disulfide linker with the aim of improving their efficacy in the absence of a transfection agent. These conjugates, especially conjugates of natural phosphodiester oligonucleotides, exhibit a reduced toxicity, an improved cell penetration efficacy and therefore an increased biological effect in inhibiting protein expression. Additionally, with respect to the shortcomings of the currently established oligonucleotide conjugate assembly routes, a facile and efficient coupling strategy was found with scale-up compatibility with the potential of being employed in the conjugation of a broad range of vectors to antisense and siRNA oligonucleotides. The functionalization of the 2'-OH-group not only provides a tether for further in-line solid-phase synthesis but also imparts nuclease stability to the conjugates and oligonucleotides according to the invention. The disulfide bond(s) present(s) in the respective conjugates according to the invention can be cleaved after cellular uptake, preventing detrimental effects of the ligands on hybridisation properties of the conjugates and oligonucleotides. Moreover, the conjugates according to the invention show significant biological effects without the addition of a cell penetration enhancer as well as exhibit high binding affinity to target RNA.

Further, it was now surprisingly found that the synthesis of 2' disulfide conjugates of t-oxo-pyrimidine nucleosides is faster by allowing easier access of the substituent to the ribose ring when an 2-2'-anhydropyrimidine nucleoside is used as an intermediate product, compared to standard synthesis pathways. Additionally, by using an 2-2'-anhydropyrimidine nucleoside, the substituent can be directly coupled to the 2' ribose position without the need of additional steps which are generally necessary in standard conjugate assembly routes such as introduction of protection groups on the hydroxygroups of the ribose ring, reduction of the substituent, and derivatization of the substituent. Therefore, the inventive synthesis of 2' disulfide conjugates of 2-oxo-pyrimidine nucleosides provides an efficient and fast synthesis pathway of the inventive conjugates.

It was also surprisingly found that an oligonucleotide, bound to a solid support and exhibiting conjugates at the 2' position of ribose rings with unprotected free thiol groups, offers an highly efficient substrate for disulfide conjugate coupling on said thiol group. This oligonucleotide is especially highly efficient when disulfide conjugate coupling on more than one thiol groups is desired.

An object of the present invention is to provide an antisense or siRNA oligonucleotide or conjugate with improved pharmacokinetic properties, methods of producing the same and producing 2' conjugates of 2-oxo-pyrimidine nucleosides as well as the use of such compounds and conjugates, e.g. as pharmaceutical composition, a pharmaceutical kit, a medicament or a tool in biomedical research.

In one aspect the present invention relates to a conjugate of formula I,

P-(L-S—S—Y—X)$_n$  (I)

wherein P represents a natural, artificial and/or modified oligonucleotide, L represents a linker group attached to one or more nucleosides at any position within the oligonucleotide sequence; S represents sulfur; X represents a ligand; Y represents a spacer and n is an integer ranging from 1 to the oligonucleotide length of P.

In addition, the invention relates to an oligonucleotide of formula II,

P-(L-S—R)$_n$  (II)

wherein P represents a natural, artificial and/or modified oligonucleotide, L represents a linker group attached to one or more nucleosides at any position within the oligonucleotide sequence, S represents sulfur, R represents either hydrogen or a thiol protecting group, preferably trityl or tertiary butyl, and n is an integer ranging from 1 to the oligonucleotide length of P.

Moreover, the invention relates to a nucleotide or nucleoside according to formula III,

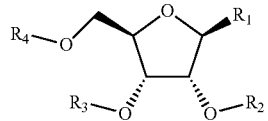

(III)

wherein R1 represents any N-protected natural or modified nucleobase; R2 represents a linear, branched, unsubstituted or halogen substituted $C_1$-$C_{10}$ alkyl chain bound to a free thiol group or to a thiol-tertiary butylsulfenyl or thiol-methane sulfonate protected group anywhere in the chain, preferably at the chain end; or a -L-S-trityl group or a -L-S—S-tertiary butyl group, wherein L represents a linker group and S represents sulfur; R3 represents a succinic ester or a phosphoramidite group or a hydrogen; and R4 represents independently hydrogen, a protecting group, a monophosphate, diphosphate or tri phosphate.

The natural, artificial and/or modified oligonucleotide P of the conjugate of the invention comprises natural, artificial and/or modified nucleosides having natural, artificial and/or modified nucleobases, wherein a number of said nucleosides form an oligonucleotide selected from the group consisting of: phosphodiester oligonucleotide (PDOs), phosphorothioate oligonucleotides (PSOs), phosphorodiamidate morpholino oligonucleotides (PMOs), peptide nucleic acids (PNAs), locked nucleic acids (LNAs), ethyl bicyclic nucleic acids (cET BNA), 2'-fluor oligonucleotides, 2'-fluor oligoarabinonucleotides and combinations thereof.

Furthermore, the invention relates in another aspect to a method of the preparation of a conjugate, a pharmaceutical composition or a pharmaceutical kit comprising the conjugate, the use of such a pharmaceutical composition as a medicament or a tool in biomedical research. Further, the pharmaceutical composition or pharmaceutical kit or conjugate can be used for the treatment of a disease or disorder that can be at least in part alleviated by therapy, wherein the disease or disorder is selected from the group consisting of bacterial infections, viral infections, cancer, metabolic diseases and immunological disorders and preferably cancer.

BRIEF DESCRIPTION OF THE DRAWING

The figures presented herewith and the attendant examples are not to be construed as limiting the invention in any way, but rather as serving only for the purpose of exemplification. The used abbreviation "PG" represents a protecting group and "B" represents a nucleobase.

DETAILED DESCRIPTION OF THE INVENTION

Figure 1A:
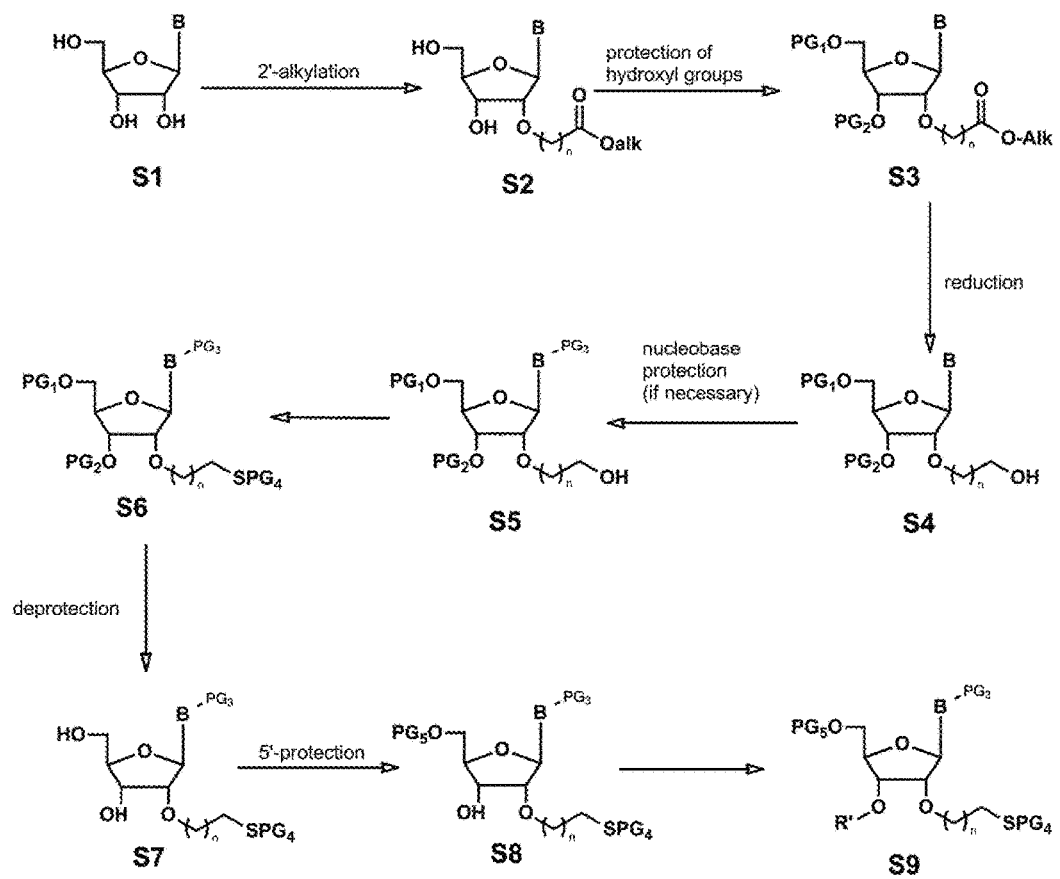
FIG. 1a shows an example of the synthesis of a S-trityl protected 2'-thiol modified nucleoside and FIG. 1b shows the detailed synthesis of a S-trityl protected 2'-thiol modified adenosine.

In one aspect of the present invention, it relates to a conjugate of formula I,

P-(L-S—S—Y—X)ₙ    (I)

wherein P represents a natural, artificial and/or modified oligonucleotide, L represents a linker group attached to one or more nucleosides at the 2 position of one or more ribose rings within the oligonucleotide sequence; S represents sulfur; X represents a ligand; Y represents a spacer and n is an integer ranging from 1 to the oligonucleotide length of P.

In another embodiment, the invention relates to an oligonucleotide of formula II,

P-(L-S—R)ₙ    (II)

wherein P represents a natural, artificial and/or modified oligonucleotide, L represents a linker group attached to one or more nucleosides at the 2 position of one or more ribose rings within the oligonucleotide sequence, S represents sulfur, R represents either hydrogen or a thiol protecting group, preferably trityl or tertiary butyl, and n is an integer ranging from 1 to the oligonucleotide length of P.

In a further embodiment, the invention relates to an oligonucleotide having the formula IV

P-(L-S—H)ₙ    (IV)

wherein the oligonucleotide is bound to a solid support and wherein,
P represents a natural, artificial and/or modified oligonucleotide,
L represents a linker group attached to one or more nucleosides at the 2' position of one or more ribose rings of the oligonucleotide within the oligonucleotide sequence;
S represents sulfur;
n is an integer ranging from 1 to the oligonucleotide length of P;
H represents hydrogen.

In the context of the invention, the term oligonucleotide refers to an oligomer or polymer of ribonucleic acid (RNA) or deoxyribonucleic acid (DNA) or mimetic thereof. This term includes oligonucleotides composed of naturally-occurring nucleobases, sugars and covalent internucleoside (backbone) linkages as well as oligonucleotides having non-naturally-occurring parts with similar functions. Such modified or substituted oligonucleotides are often preferred over native forms because of desirable properties such as, for example, enhanced cellular uptake, enhanced affinity for nucleic acid targets and increased stability in the presence of nucleases.

While antisense oligonucleotides are a preferred form of antisense compounds, the present invention comprehends other oligomeric compounds useful in antisense applications, including but not limited to oligonucleotide mimetics such as are described below. The antisense compounds in accordance with this invention preferably comprise from about 8 to about 80 nucleobases (i.e. from about 8 to about 80 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is usually a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked either to the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

The natural, artificial and/or modified oligonucleotide P of the conjugate according to formula I, the oligonucleotide according to formula II or the oligonucleotide according to formula IV of the invention comprises natural, artificial and/or modified nucleosides having natural, artificial and/or modified nucleobases, wherein a number of said nucleosides form an oligonucleotide selected preferably from the group consisting of: phosphodiester oligonucleotide (PDOs), phosphorothioate oligonucleotides (PSOs), phosphorodiamidate morpholino oligonucleotides (PMOs), peptide nucleic acids (PNAs), locked nucleic acids (LNAs), ethyl bicyclic nucleic acids (cET BNA), 2'-fluor oligonucleotides, 2'-fluor oligoarabinonucleotides, and combinations thereof.

In one embodiment P is a natural oligonucleotide having an oligonucleotide sequence that is complementary to an oligonucleotide sequence encoding for the apoptosis-regulating proteins, in particular clusterin, survivin and Bcl-2. Those apoptosis-regulating proteins are in particular encoded by the CLU gene (clusterin), BIRC5 gene (survivin) and the Bcl-2 gene.

The linker L of the conjugate according to formula I, the oligonucleotide according to formula II, the nucleotide/nucleoside according to formula III or the oligonucleotide according to formula IV preferably represents a linear alkyl linker of 1 to about 10 carbon atoms, more preferably of 2 to about 6 carbon atoms, more preferably of 2 carbon atoms or a polyethylene glycol linker of 1 to about 20 ethylene glycol units, preferably 2 to about 12 ethylene glycol units.

The linker L of the conjugates according to formula I, the oligonucleotides according to formula II or the oligonucleotide according to formula IV of the invention is covalently linked at any position within the oligonucleotide sequence, preferably via the oxygen atom to the 2' position of the ribose ring of a phosphodiester oligonucleotide, a phosphorothioate oligonucleotide, at the 2' position of the morpholine ring of a phosphorodiamidate morpholino oligonucleotide, or an equivalent position of a peptide nucleic acid.

In one embodiment, the oligonucleotide according to formula IV is bound to solid support. Said solid support can be any resin suitable to bind oligonucleotides. In a preferred embodiment, the solid support is the aminofunctionalized LCAA-CPG (Long Chain Amino Alkyl Controlled Pore Glass) resin.

In one embodiment, the ligand X of the conjugate of formula I of the invention is selected from the group consisting of peptides of 1 to about 40 amino acids, preferably peptides with more than about 20% arginine or lysine amino acids and natural basic peptides such as protamine, more preferably peptides with more than about 50% arginine or lysine amino acids, and natural basic peptides such as protamine. The amino acids means at least one amino acid can be a L- or D-amino acid or if more than one also a mixture of L- and D-amino acids. In another preferred embodiment, the ligand X is selected from peptides known to enhance cellular uptake or intracellular transport, such as HIV TAT-1, penetratin, and other cell penetrating peptides and protein transduction domains (PTDs). In another preferred embodiment the ligand X comprises 2 to 20 lysine amino acids, preferably 3 to 15, most preferably 3 to 9 lysine amino acids, such as 3, 4, 5, or 6 lysine amino acids.

In another embodiment, the ligand X is selected from the group consisting of linear and branched, preferably linear, polyethylene glycols of 2 to about 200 ethylene glycol units, preferably 2 to about 50 ethylene glycol units, more preferably 2 to about 24 ethylene glycol units and most preferably of 3 to 9 ethylene glycol units. The polyethylene glycol units may be terminated by a methyl group, a hydroxyl group or any other residue that is chemically compatible with the use of the molecule and preferably is a methyl group.

In a further embodiment the ligand X is a polymer with basic charges at neutral or acidic pH, including polyamines, linear and branched polyethylene imines; or a lipophilic compound, e.g. cholesterol or lipid acids like stearic acid, linoleic acid, etc. or tocopherol. A ligand, exhibiting positive charges such as peptides with arginine, lysine, and/or protamine, amphiphilic structures, such as polyethylene glycol, peptides for cellular uptake or intracellular transport, polymers with basic charges at neutral or acidic pH or lipophilic compounds and bound to the conjugate, increases the uptake of the conjugate into the cell and is therefore advantageous for an efficient cellular uptake. Further, ligands for receptor-specific interactions, comprising N-acetyl galactosamine, folic acid, anisamide, receptor-specific peptides (RVG, RGD, etc.), antibodies, antibody derivatives and antibody fragments, and other protein scaffolds, including affibodies, anticalins, monobodies, ankyrin repeat proteins, armadillo repeat proteins and avimers increase the uptake of the conjugate into the cell.

In one embodiment the spacer Y is a —$(CH_2)_m$—$NH_2$—CO— group, wherein m is an integer of 1 to 6, in particular a carbonyl amino methyl, a carbonyl amino ethyl, a carbonyl amino butyl, a carbonyl amino propyl group, a carbonyl amino pentyl or a carbonyl amino hexyl group.

In another embodiment the spacer Y is an alkyl group having 1 to 6 carbon atoms, preferably a linear alkyl group, in particular a methyl, ethyl, n-butyl or n-propyl, n-pentyl or n-hexyl group.

In one embodiment in the structural element —S—Y—X— of formula (I) S means a sulfur atom, (Y+X) means the spacer Y and the ligand X together is a [cysteinyl-S-yl]-polylysine residue, preferably having 1 to 9 lysine amino residues. In this respect [cysteinyl-S-yl] is understood as being a —S—$CH_2$—$CH(NH_2)$—CO— residue. In this respect the amino acids may be a L- or D-amino acid or a mixture thereof.

In another embodiment in the structural element —S—Y—X— of formula (I) S that means a sulfur atom, (Y+X) means the spacer Y and the ligand X together is a —$CH_2$-(PEG)q unit, wherein PEG is a polyethylene glycol unit and q is an integer of 1 to about 200, preferably with 2 to about 50 units, more preferably 2 to about 24 units and most preferably of 3 to 9 units.

The oligonucleotide length of P of the conjugate according to formula I or the oligonucleotide according to formula II is preferably about 8 to about 80 nucleotides, more preferably 10 to 30 nucleotides, most preferably 16 to 24 nucleotides.

In one embodiment of the invention the conjugate according to formula I comprises at least one linker L that represents a $C_2$ to $C_{10}$ alkyl linker, preferably ethyl, and the ligand X represents a polylysine, preferably having 3 to 6 lysine amino acid units or a polyethylene glycol having preferably 3 to 9 ethylene glycol units; and the spacer Y represents a carbonyl amino methyl or a carbonyl amino ethyl group, i.e. a —$(CH_2)$—$NH_2$—CO— group or a —$(CH_2)_2$—$NH_2$—CO— group, preferably a carbonyl amino methyl group.

In another embodiment of the invention the linker L of the conjugate according to formula I of the invention represents a polyethylene glycol linker of 1 to about 20 ethylene glycol units and the ligand X represents a ligand for receptor-specific interactions, including N-acetyl galactosamine, folic acid, anisamide, receptor-specific peptides (RVG, RGD, etc.), antibodies, antibody derivatives and antibody fragments, and other protein scaffolds, including affibodies, anticalins, monobodies, ankyrin repeat proteins, armadillo repeat proteins and avimers; and the spacer Y represents a carbonyl amino methyl or a carbonyl amino ethyl group, i.e. a —$(CH_2)$—$NH_2$—CO— group or a —$(CH_2)_2$—$NH_2$—CO— group, preferably a carbonyl amino methyl group.

In a preferred embodiment, the conjugate according to formula I of the invention represents a conjugate, wherein P represents a natural oligonucleotide, the conjugate having at least one linker L, wherein the linker L represents an ethyl linker that is attached via the 2'-OH group to the oligonucleotide, the ligand X represents a polylysine residue having 1 to 40 lysine amino acids units having a free amino terminal function, preferably a 3 to 9 lysine amino acid unit or a ligand X that represents a polyethylene glycol having 2 to 20 ethylene glycol units, preferably 2 to 9 ethylene glycol units; and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group. The number of nucleotides of the natural oligonucleotide in the conjugate is about 8 to about 80 nucleotides, preferably 10 to 30 nucleotides, more preferably 16 to 24 oligonucleotides.

In another embodiment of the invention, the conjugate according to formula I represents a conjugate, wherein P represents a natural oligonucleotide, the conjugate having at least one linker L, wherein the linker L represents an ethyl linker that is attached via the 2'-OH group to the oligonucleotide, the ligand X and spacer Y together represents an amino acid sequence wherein a C-terminal cysteine for coupling is followed by a polylysine residue having 1 to 40 lysine amino acids units having a free amino terminal function, preferably a 3 to 9 lysine amino acid unit or the ligand X and spacer Y together represent a structural unit comprising a methyl, ethyl or n-butyl group and a polyethylene glycol having 2 to 20 ethylene glycol units, preferably 2 to 9 ethylene glycol units. The number of nucleotides of the natural oligonucleotide in said conjugate is about 8 to about 80 nucleotides, preferably 10 to 30 nucleotides, more preferably 16 to 24 oligonucleotides.

In a preferred embodiment, the oligonucleotide according to formula II, i.e. P-(L-S—R)$_n$ of the invention represents an oligonucleotide, wherein P represents a natural oligonucleotide, the conjugate having at least one linker L, wherein the linker L represents an ethyl linker that is attached via the 2'-OH group to the oligonucleotide and the residue R represents hydrogen or a thiol protecting group, preferably a trityl or a tertiary butyl group. Of course, during synthesis the oligonucleotide according to formula II may also contain any protecting groups of any functional group contained in the oligonucleotide structure known to the skilled person in the art. The number of nucleotides of the oligonucleotide of the invention is about 8 to about 80 nucleotides, preferably 10 to 30 nucleotides, more preferably 16 to 24 oligonucleotides.

In another embodiment the invention relates to a nucleotide or nucleoside according to formula III,

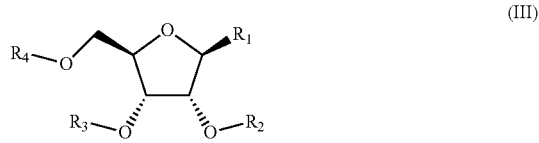

(III)

wherein R1 represents any N-protected natural or modified nucleobase; R2 represents a linear, branched, unsubstituted or halogen substituted $C_1$-$C_{10}$ alkyl chain bound to a free thiol group or to a thiol-tertiary butylsulfenyl or thiol-methane sulfonate protected group anywhere in the chain, preferably at the chain end; or a -L-S-trityl group or a -L-S—S-tertiary butyl group, wherein L represents a linker group and S represents sulfur; R3 represents a succinic ester or a phosphoramidite group or a hydrogen; and R4 represents independently hydrogen, a protecting group, a monophosphate, diphosphate or triphosphate. Of course, during synthesis the nucleoside according to formula III may also contain any protecting groups of any functional group contained in the nucleoside structure known to the skilled person in the art. The linker group L as present in the R2 residue represents a linear alkyl linker of 1 to about 10 carbon atoms, preferably of 2 to about 6 carbon atoms, more preferably of 2 carbon atoms or a polyethylene glycol linker of 1 to about 20 ethylene glycol units, preferably 2 to about 12 ethylene glycol units.

In a preferred embodiment the nucleotide or nucleoside according to formula III comprises a residue R1 being any N-protected natural or modified nucleobase, R2 represents a -L-S-trityl or a -L-S—S-tertiary butyl group, wherein the linker L is a linear C2 group, i.e. an ethyl group, R3 represents a succinic ester for direct coupling to the solid support or a phosphoramidite for internal couplings or a hydrogen, preferably a succinic ester or a phosphoramidite, and R4 represents independently a hydrogen, a protecting group, a monophosphate, diphosphate or triphosphate, preferably hydrogen or a protecting group, in particular a dimethoxytrityl group.

The conjugate according to formula I or the oligonucleotide according to formula II may comprise one or more additional linkers L' and in addition the conjugate may further comprise one or more additional ligands X' and one or more additional spacers Y' at the 2'-O—, 3'-O—, and 5'-O-positions of the oligonucleotide or nucleoside, e.g. aminoalkyl linkers, azide linkers, alkinyl linkers or other linkers commonly used for ligand attachment for convergent dual ligand attachments.

In a conjugate, oligonucleotide or nucleoside according to the invention the additional linker L' is selected from the group consisting of a linear alkyl linker of 1 to 10 carbon atoms, preferably of 2 to about 6 carbon atoms, more preferably of 2 carbon atoms, a polyethylene glycol linker of 1 to about 20 ethylene glycol units, preferably 2 to 12 ethylene glycol units. The additional ligand X' of the conjugate is a dye, a fluorescence dye, a fluorescence marker or being a ligand X. The one or more additional spacer Y' is a —(CH$_2$)$_m$—NH$_2$—CO— group, wherein m is an integer of 1 to 6, in particular a carbonyl amino methyl, a carbonyl amino ethyl, a carbonyl amino butyl, a carbonyl amino propyl group, a carbonyl amino pentyl or a carbonyl amino hexyl group. In another embodiment the spacer Y is an alkyl group having 1 to 6 carbon atoms, preferably a linear alkyl group, in particular a methyl, ethyl, n-butyl or n-propyl, n-pentyl or n-hexyl group.

Methods of Preparation

The invention relates also to a method for the preparation of a conjugate according to formula I of the invention having the following structure P-(L-S—S—Y—X)$_n$ (I)

comprising the following steps of
reacting the compound P-(L-S—H)$_n$ having the formula IV with the respective equivalents, preferably 1 to 10 equivalents, of a methane thiosulfonate or HO—SO$_2$—S—Y—X containing compound in solution phase or solid phase. In the formula I according to invention P represents a natural, artificial and/or modified oligonucleotide; L represents a linker group attached to one or more nucleosides at any position within the oligonucleotides sequence; S represents sulfur; X represents a ligand; Y represents a spacer and n is an integer ranging from 1 to the oligonucleotide length of P.

In the formula HO—SO$_2$—S—Y—X S represents sulfur; O represents oxygen; H represents hydrogen; X represents a ligand; Y represents a spacer having the same meaning as described in connection with the conjugate i.e. the compound according to formula I of the present invention.

The terms "oligonucleotide" and "nucleosides" etc. have the same meaning as defined above in connection with the compounds, conjugates, oligonucleotides and nucleosides.

The natural, artificial and/or modified oligonucleotide P of the conjugate according to formula I or the oligonucleotide according to formula IV of the invention comprises natural, artificial and/or modified nucleosides having natural, artificial and/or modified nucleobases, wherein a number of said nucleosides form an oligonucleotide selected preferably from the group consisting of: phosphodiester oligonucleotide (PDOs), phosphorothioate oligonucleotides (PSOs), phosphorodiamidate morpholino oligonucleotides (PMOs), peptide nucleic acids (PNAs), locked nucleic acids (LNAs), ethyl bicyclic nucleic acids (cET BNA), 2'-fluor oligonucleotides, 2'-fluoro oligoarabinonucleotides or a combination thereof.

In one embodiment P is a natural oligonucleotide having an oligonucleotide sequence that is complementary to an oligonucleotide sequence encoding for the apoptosis-regulating proteins, in particular clusterin, survivin and Bcl-2. Those apoptosis-regulating proteins are in particular encoded by the CLU gene (clusterin), BIRC5 gene (survivin) and the Bcl-2 gene.

The linker L of the conjugate according to formula I, the oligonucleotide according to formula II and IV represents a linear alkyl linker of 1 to about 10 carbon atoms, preferably of 2 to about 6 carbon atoms, more preferably of 2 carbon atoms or a polyethylene glycol linker of 1 to about 20 ethylene glycol units, preferably 2 to about 12 ethylene glycol units.

The linker L of the conjugates according to formula I or the oligonucleotides according to formula IV of the invention is covalently linked at any position within the oligonucleotide sequence, preferably via the oxygen atom to the 2' position of the ribose ring of a phosphodiester oligonucleotide, a phosphorothioate oligonucleotide, at the 2' position of the morpholine ring of a phosphorodiamidate morpholino oligonucleotide, or an equivalent position of a peptide nucleic acid.

In one embodiment, the ligand X of the conjugate of formula I or in the formula HO—SO$_2$—S—Y—X is selected from the group consisting of peptides of 1 to about 40 amino acids, preferably peptides with more than about 20% arginine or lysine amino acids and natural basic peptides such as protamine, more preferably peptides with more than about 50% arginine or lysine amino acids, and natural basic peptides such as protamine. The amino acids means at least one amino acid can be a L- or D-amino acid or if more than one also a mixture of L- and D-amino acids. In another preferred embodiment, the ligand X is selected from peptides known to enhance cellular uptake or intracellular transport, such as HIV TAT-1, penetratin, and other cell penetrating peptides and protein transduction domains (PTDs). In another preferred embodiment the ligand X comprises 2 to 20 lysine amino acids, preferably 3 to 15, most preferably 3 to 9 lysine amino acids.

In another embodiment, the ligand X of the conjugate of formula I or formula HO—SO$_2$—S—Y—X is selected from the group consisting of linear and branched, preferably linear, polyethylene glycols of 2 to about 200 ethylene glycol units, preferably 2 to about 50 ethylene glycol units, more preferably 2 to about 24 ethylene glycol units and most preferably of 3 to 6 ethylene glycol units. The polyethylene glycol units may be terminated by a methyl group, a hydroxyl group or any other residue that is chemically compatible with the use of the molecule and preferably is a methyl group.

In a further embodiment the ligand X of the conjugate of formula I or formula HO—SO$_2$—S—Y—X is a polymer with basic charges at neutral or acidic pH, including polyamines, linear and branched polyethylene imines; or a lipophilic compound, e.g. cholesterol or lipid acids like stearylic acid, linolic acid, etc. or tocopherol.

In one embodiment the spacer Y is a —(CH$_2$)$_m$—NH$_2$—CO— group, wherein m is an integer of 1 to 6, in particular a carbonyl amino methyl, a carbonyl amino ethyl, a carbonyl amino butyl, a carbonyl amino propyl group, a carbonyl amino pentyl or a carbonyl amino hexyl group.

In another embodiment the spacer Y is an alkyl group having 1 to 6 carbon atoms, preferably a linear alkyl group, in particular a methyl, ethyl, n-butyl or n-propyl, n-pentyl or n-hexyl group.

In one embodiment in the structural element —S—Y—X— of formula (I) S means a sulfur atom, (Y+X) means the spacer Y and the ligand X together is a [cysteinyl-S-yl]-polylysine residue, preferably having 1 to 9 lysine amino residues. In this respect [cysteinyl-S-yl] is understood as being a —S—CH$_2$—CH(NH$_2$)—CO— residue. In this respect the amino acids may be a L- or D-amino acid or a mixture thereof.

In another embodiment in the structural element —S—Y—X— of formula (I) S means a sulfur atom, (Y+X) means the spacer Y and the ligand X together is a —CH$_2$-(PEG)q unit, wherein PEG is a polyethylene glycol unit and q is an integer of 1 to about 200, preferably with 2 to about 50 units, more preferably 2 to about 24 units and most preferably of 3 to 9 units and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group.

The number n ranging from 1 to the number of nucleotides in the conjugate according to formula I or the oligonucleotide according to formula II is typically 1, but may also range from 1 to the length of the oligonucleotide P, preferably 1 to 10, most preferably 1 to 6.

In one embodiment of the invention the conjugate according to formula I comprises at least one linker L that represents a C$_2$ to C$_{10}$ alkyl linker, preferably ethyl, and the ligand X represents a polylysine, preferably having 3 to 6 lysine amino acid units or a polyethylene glycol having preferably 3 to 9 ethylene glycol units; and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group.

In another embodiment of the invention the linker L of the conjugate according to formula I of the invention represents a polyethylene glycol linker of 1 to about 20 ethylene glycol units and the ligand X represents a ligand for receptor-specific interactions, including N-acetyl galactosamine, folic acid, anisamide, receptor-specific peptides (RVG, RGD, etc.), antibodies, antibody derivatives and antibody fragments, and other protein scaffolds, including affibodies, anticalins, monobodies, ankyrin repeat proteins, armadillo repeat proteins and avimers; and the spacer Y represents a carbonyl amino methyl or a carbonyl amino ethyl group, i.e.

a —(CH$_2$)—NH$_2$—CO— group or a —(CH$_2$)$_2$—NH$_2$—CO— group, preferably a carbonyl amino methyl group.

In a preferred embodiment, the conjugate according to formula I of the invention represents a conjugate, wherein P represents a natural oligonucleotide, the conjugate having at least one linker L, wherein the linker L represents an ethyl linker that is attached via the 2'-OH group to the oligonucleotide, the ligand X represents a polylysine residue having 1 to 40 lysine amino acids units having a free amino terminal function, preferably a 3 to 9 lysine amino acid unit or a ligand X that represents a polyethylene glycol having 2 to 20 ethylene glycol units, preferably 2 to 9 ethylene glycol units; and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group. The number of nucleotides of the natural oligonucleotide in the conjugate is about 8 to about 80 nucleotides, preferably 10 to 30 nucleotides, more preferably 16 to 24 oligonucleotides.

In another embodiment of the invention, the conjugate according to formula I represents a conjugate, wherein P represents a natural oligonucleotide, the conjugate having at least one linker L, wherein the linker L represents an ethyl linker that is attached via the 2'-OH group to the oligonucleotide, the ligand X and spacer Y together (Y+X) represents an amino acid sequence wherein a C-terminal cysteine for coupling is followed by a polylysine residue having 1 to 40 lysine amino acids units having a free amino terminal function, preferably a 3 to 9 lysine amino acid unit or the ligand X and spacer Y together (Y+X) represent a structural unit comprising a methyl, ethyl or n-butyl group and a polyethylene glycol having 2 to 20 ethylene glycol units, preferably 2 to 9 ethylene glycol units. The number of nucleotides of the natural oligonucleotide in said conjugate is about 8 to about 80 nucleotides, preferably 10 to 30 nucleotides, more preferably 16 to 24 oligonucleotides.

Further, the invention relates to a method for the preparation of a compound according to formula IV P-(L-S—H)$_n$         (IV)

wherein the method comprises the step of removing one or more protecting groups from the thiol group of a compound P-(L-S—R)$_n$ according to formula II with silver nitrate followed by addition of dithiothreitrol; or tributylphosphine treatment, depending on the protecting group, or alternatively if R already represents hydrogen in the compound P-(L-S—R)$_n$ that corresponds to formula IV; reacting the compound with dithiothreitrol in order to obtain the respective free thiol compound, wherein P represents a natural, artificial and/or modified oligonucleotide, L represents a linker group attached to one or more nucleosides at any position within the oligonucleotides sequence; S represents sulfur; and n is an integer ranging from 1 to the oligonucleotide length of P and R represents a thiol protecting group, preferably a trityl group or a tertiary butyl group.

The invention also relates to a method for the preparation of 2-oxo-pyrimidine nucleoside 2' conjugates, wherein the method comprises reacting a 2-2'-anhydropyrimidine nucleoside with a compound having the formula V (U1-O-L-S-U2)         (V)

wherein U1 represents a protecting group, O represents oxygen, L represents a linker, S represents sulfur and U2 represents a protecting group.

In a embodiment, the U1 protecting group is preferably selected from any silyl protecting group such as trimethylsilyl, triethylsilyl, tert-butyldiphenylsilyl, tert-butyldimethylsilyl, tert-butylsilyl, methyldiisopropylsilyl, triphenylsilyl and triisopropylsilyl.

In a further embodiment, the U2 protecting group is selected from 2-thiopyridine, 4-thiopyridine, phenylselenyl, thioethyl, thiophenyl, 2-(4-pyridyl)ethyl, triphenylmethyl, diphenylmethyl, 4,4'-dimethoxydiphenylmethyl, acetamidomethyl, trityl, tert-butyl.

Preferably, the U2 protecting group is selected from 2-thiopyridine, 4-thiopyridine, and phenylselenyl.

The linker L of the conjugate according to formula V represents a linear alkyl linker of 1 to about 10 carbon atoms, preferably of 2 to about 6 carbon atoms, more preferably of 2 carbon atoms or a polyethylene glycol linker of 1 to about 20 ethylene glycol units, preferably 2 to about 12 ethylene glycol units.

The 2-oxo-pyrimidine nucleoside can be any natural, artificial or modified pyrimidine nucleobase which exhibit a keto group at the 2 position.

In the present method for the preparation of the conjugate according to formula I or the oligonucleotide according to formula II or IV the substituents have the same meaning as mentioned in the chapter of the respective compounds and the methods before.

The method for the preparation of a conjugate according to the formula I can be carried out in solution or in solid phase synthesis.

In one embodiment, a method for the preparation of a conjugate P-(ethyl-S—S—Y—X)$_n$ according to the following formula is shown,

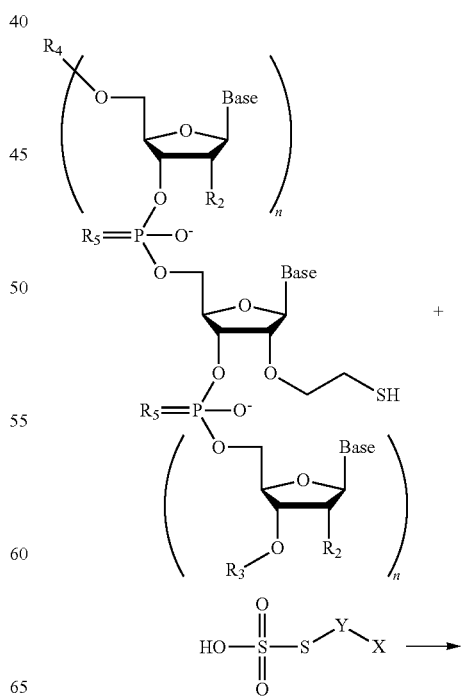

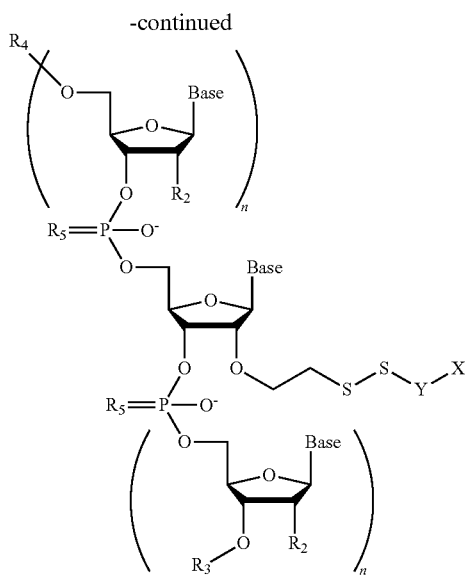

wherein P represents a natural oligonucleotide having natural nucleobases, the ligand X of said conjugate or in the formula HO—SO$_2$—S—Y—X is selected from the group consisting of peptides of 1 to about 40 amino acids, preferably peptides with more than about 20% arginine or lysine amino acids and natural basic peptides such as protamine, more preferably peptides with more than about 50% arginine or lysine amino acids, and natural basic peptides such as protamine. The amino acids means at least one amino acid can be a L- or D-amino acid or if more than one also a mixture of L- and D-amino acids.

In another preferred embodiment, the ligand X is selected from peptides known to enhance cellular uptake or intracellular transport, such as HIV TAT-1, penetratin, and other cell penetrating peptides and protein transduction domains (PTDs). In another preferred embodiment the ligand X comprises 2 to 20 lysine amino acids, preferably 3 to 15, most preferably 3 to 9 lysine amino acids.

In another embodiment, the ligand X of said conjugate or formula HO—SO$_2$—S—Y—X is selected from the group consisting of linear and branched, preferably linear, polyethylene glycols of 2 to about 200 ethylene glycol units, preferably 2 to about 50 ethylene glycol units, more preferably 2 to about 24 ethylene glycol units and most preferably of 3 to 6 ethylene glycol units. The polyethylene glycol unit may be terminated by a methyl group, a hydroxyl group or any other residue that is chemically compatible with the use of the molecule and preferably is a methyl group.

In a further embodiment the ligand X of said conjugate or formula HO—SO$_2$—S—Y—X is a polymer with basic charges at neutral or acidic pH, including polyamines, linear and branched polyethylene imines; or a lipophilic compound, e.g. cholesterol or lipid acids like stearylic acid, linolic acid, etc. or tocopherol.

In one embodiment the spacer Y of said conjugate or the formula HO—SO$_2$—S—Y—X is a —(CH$_2$)$_m$—NH$_2$—CO— group, wherein m is an integer of 1 to 6, in particular a carbonyl amino methyl, a carbonyl amino ethyl, a carbonyl amino butyl, a carbonyl amino propyl group, a carbonyl amino pentyl or a carbonyl amino hexyl group.

In another embodiment the spacer Y is an alkyl group having 1 to 6 carbon atoms, preferably a linear alkyl group, in particular a methyl, ethyl, n-butyl or n-propyl, n-pentyl or n-hexyl group.

In one embodiment in the structural element —S—Y—X— of those formulae S means a sulfur atom, (Y+X) means the spacer Y and the ligand X together is a [cysteinyl-S-yl]-polylysine residue, preferably having 1 to 9 lysine amino residues. In this respect [cysteinyl-S-yl] is understood as being a —S—CH$_2$—CH(NH$_2$)—CO— residue. In this respect the amino acids may be a L- or D-amino acid or a mixture thereof.

In another embodiment in the structural element —S—Y—X— of those formulae S means a sulfur atom, (Y+X) means the spacer Y and the ligand X together is a —CH$_2$-(PEG)q unit, wherein PEG is a polyethylene glycol unit and q is an integer of 1 to about 200, preferably with 2 to about 50 units, more preferably 2 to about 24 units and most preferably of 3 to 9 units and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group.

The number of nucleotides of said conjugate or said oligonucleotide is about 8 to about 80 nucleotides, preferably 10 to 30 nucleotides, most preferably 16 to 24 nucleotides.

Further, in the above mentioned formula, R2 represents H, —OH, a protecting group or a linker group L; R3 represents H, an oligonucleotide or a linker group L; R4 represents H, an oligonucleotide, a phosphate or a linker group L; and R5 represents an oxygen or sulfur atom; and X represents a ligand.

The synthesis can be performed in solution or in solid phase, preferably in solution.

In another embodiment the method for the preparation of a conjugate according to the below formula can be carried out in solution or solid phase, preferably in solid phase with a solid-supported oligonucleotide according to the following general procedure:

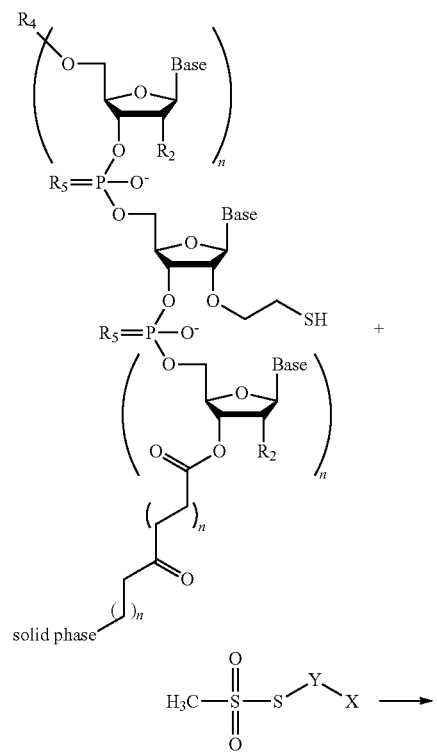

-continued

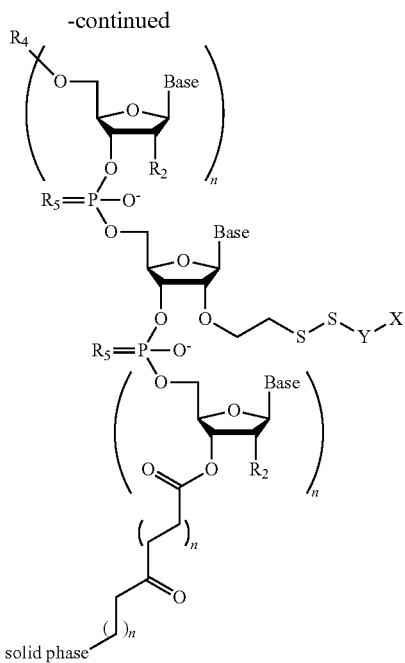

wherein P represents a natural oligonucleotide having natural nucleobases, the ligand X of said conjugate or in the formula HO—SO$_2$—S—Y—X is selected from the group consisting of peptides of 1 to about 40 amino acids, preferably peptides with more than about 20% arginine or lysine amino acids and natural basic peptides such as protamine, more preferably peptides with more than about 50% arginine or lysine amino acids, and natural basic peptides such as protamine. The amino acids means at least one amino acid can be a L- or D-amino acid or if more than one also a mixture of L- and D-amino acids. In another preferred embodiment, the ligand X is selected from peptides known to enhance cellular uptake or intracellular transport, such as HIV TAT-1, penetratin, and other cell penetrating peptides and protein transduction domains (PTDs). In another preferred embodiment the ligand X comprises 2 to 20 lysine amino acids, preferably 3 to 15, most preferably 3 to 9 lysine amino acids.

In another embodiment, the ligand X of said conjugate or formula HO—SO$_2$—S—Y—X is selected from the group consisting of linear and branched, preferably linear, polyethylene glycols of 2 to about 200 ethylene glycol units, preferably 2 to about 50 ethylene glycol units, more preferably 2 to about 24 ethylene glycol units and most preferably of 3 to 6 ethylene glycol units. The polyethylene glycol unit may be terminated by a methyl group, a hydroxyl group or any other residue that is chemically compatible with the use of the molecule and preferably is a methyl group.

In a further embodiment the ligand X of said conjugate or formula HO—SO$_2$—S—Y—X is a polymer with basic charges at neutral or acidic pH, including polyamines, linear and branched polyethylene imines; or a lipophilic compound, e.g. cholesterol or lipid acids like stearylic acid, linolic acid, etc. or tocopherol.

In one embodiment the spacer Y of said conjugate or the formula HO—SO$_2$—S—Y—X is a —(CH$_2$)$_m$—NH$_2$—CO— group, wherein m is an integer of 1 to 6, in particular a carbonyl amino methyl, a carbonyl amino ethyl, a carbonyl amino butyl, a carbonyl amino propyl group, a carbonyl amino pentyl or a carbonyl amino hexyl group.

In another embodiment the spacer Y is an alkyl group having 1 to 6 carbon atoms, preferably a linear alkyl group, in particular a methyl, ethyl, n-butyl or n-propyl, n-pentyl or n-hexyl group.

In one embodiment in the structural element —S—Y—X— of those formulae S means a sulfur atom, (Y+X) means the spacer Y and the ligand X together is a [cysteinyl-S-yl]-polylysine residue, preferably having 1 to 9 lysine amino residues. In this respect [cysteinyl-S-yl] is understood as being a —S—CH$_2$—CH(NH$_2$)—CO— residue. In this respect the amino acids may be a L- or D-amino acid or a mixture thereof.

In another embodiment in the structural element —S—Y—X— of those formulae S means a sulfur atom, (Y+X) means the spacer Y and the ligand X together is a —CH$_2$-(PEG)q unit, wherein PEG is a polyethylene glycol unit and q is an integer of 1 to about 200, preferably with 2 to about 50 units, more preferably 2 to about 24 units and most preferably of 3 to 9 units and the spacer Y represents a carbonyl amino methyl or a carbonyl amino ethyl group, i.e. a —(CH$_2$)—NH$_2$—CO— group or a —(CH$_2$)$_2$—NH$_2$—CO— group, preferably a carbonyl amino methyl group.

The number of nucleotides of said conjugate or said oligonucleotide is about 8 to about 80 nucleotides, preferably 10 to 30 nucleotides, most preferably 16 to 24 nucleotides.

Further, in the above mentioned formula, R2 represents H, —OH, a protecting group or a linker group L; R4 represents H, an oligonucleotide or a linker group L; and R5 represents an oxygen or sulfur atom; and X represents a ligand.

For the preparation of the conjugate according to the invention the nucleotide or nucleoside according to formula III

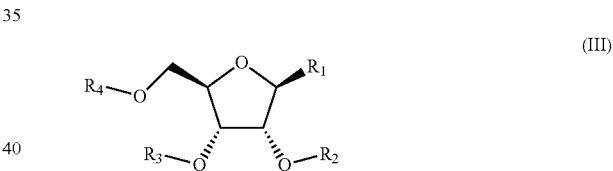

is used, wherein

R1 represents any N-protected or unprotected, natural or modified nucleobase; preferably adenine (A), guanine (G), cytosine (C), thymine (T) or uracil (U).

R2 represents a linear, branched, unsubstituted or halogen substituted C$_1$-C$_{10}$ alkyl chain bound to a free thiol group or to an thiol-tertiary butylsulfenyl or thiol-methane sulfonate protected group anywhere in the chain, preferably at the chain end; or a -L-S-trityl group or a -L-S—S-tertiary butyl group, wherein L represents a linker group and S represents sulfur;

R3 represents a succinic ester or a phosphoramidite group or a hydrogen; and

R4 represents independently hydrogen, a protecting group, a monophosphate, diphosphate or triphosphate.

In the following the synthesis of a nucleotide or nucleoside having a natural nucleobase, R2 represents a —O-linker L-group, wherein the linker L represents a linear C$_1$ to C$_{10}$ alkyl chain bound to a thiol-tertiary butylsulfenyl or thiol methane sulfonate protected group; R3 represents a hydrogen, a phosphoramidite group or a succinic ester; and R4 represents independently a hydrogen, a protecting group, a monophosphate —P(O)(OH)$_2$, diphosphate —P(O)(OH)—O—P(O)—(OH)$_2$ or triphosphate —P(O)(OH)—O—P(O)(OH)—O—P(O)(OH)$_2$, preferably a protecting group.

Figure 1B:
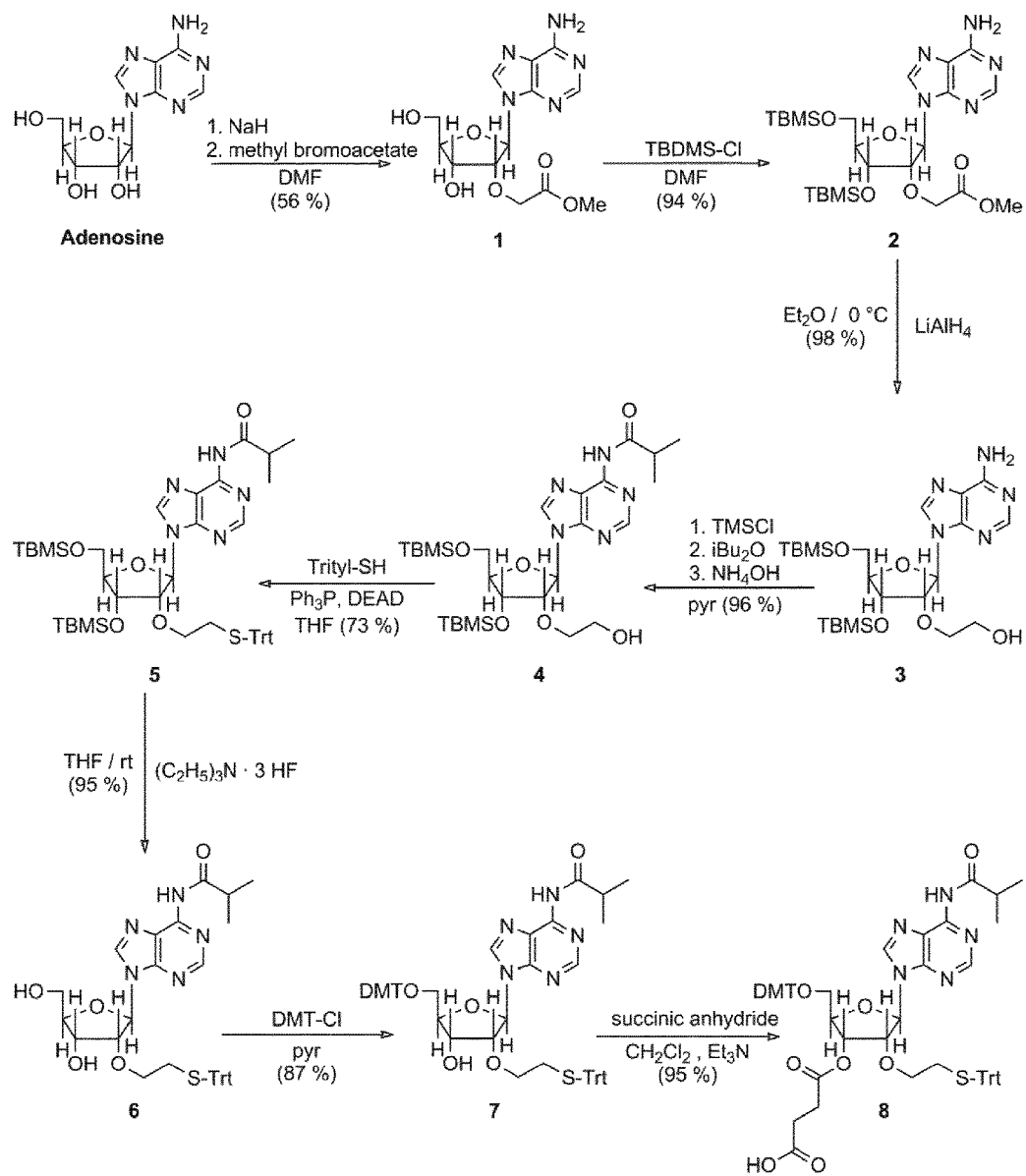

As an embodiment of the invention 2'-thiol modified nucleosides as shown in FIGS. 1a and 1b are synthesized.

In order to synthesize 2'-thiol modified nucleosides an alkylation at the 2' position was performed at the outset with an unprotected nucleobase (FIG. 1a and FIG. 1b). Due to stereoelectronic effects in nucleosides, the 2' position is rather refractory to different reactions. Therefore, alkyl chains bearing a strong electrophilic center such as alpha-bromo esters should produce more promising results with respect to yield and ease of isomers separation. The compound S1 as shown in FIG. 1a was alkylated preferentially at the 2'-position after deprotonation using, e.g sodium hydride followed by addition of methyl bromoacetate as the preliminary alkyl side chain to provide S2.

In the next step, the 3' and 5' hydroxyl groups were protected, e.g with tert-butyldimethylsilyl group, and the ester function was reduced subsequently with a reducing reagent, e.g. LiAlH$_4$, to obtain S4. The resulting 2-hydroxyalkyl e.g. 2-hydoxyethyl, side chain provides an ideal platform for carrying out further derivatizations. Protection of the exocyclic amino group (as isobutyryl amide) was performed after transient protection of the 2'-tethered hydroxyl group with trimethylsilyl chloride to afford S5. The key compound S5 obtained possesses the potential of being used for various derivatizations through displacement of the hydroxyl group with appropriate nucleophiles to create various derivatives such as 2'-amine, 2'-thiol or to carry out various conjugations such as chain elongation.

However, with respect to solid-phase conjugation approach, S-trityl protection strategy bears some shortcomings. In addition to the S-detritylation with heavy-metal ions which does not comply with solid-phase synthetic requirements, deprotection of S-triphenylmethyl thioethers can also occur through oxidative reaction with thiocyanogen, (SCN)$_2$, iodine or sulfenyl chloride to a disulfide followed by reductive cleavage to a free thiol, or under acidic conditions that is associated with the risk of depurination.

In order to create a modified nucleoside suitable for orthogonal resin-bound deprotection with the aim of creating an efficient building block for post- and/or pre-synthetic disulfide exchange reactions, advantage was taken of tert-butylsulfenyl (tbs) protection strategy.

Figure 2A:
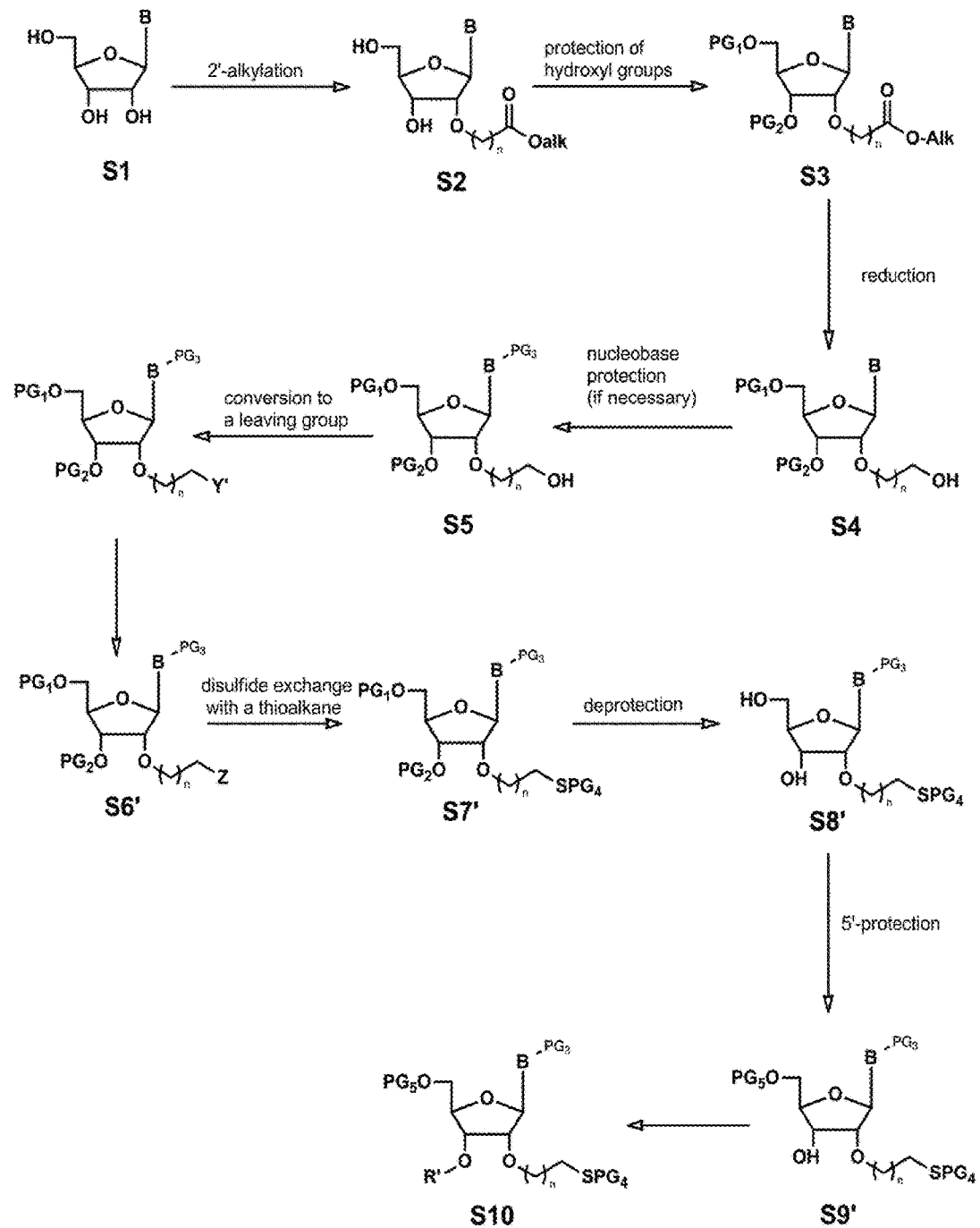
FIG. 2a shows an example of the synthesis of the S-tert-butylsulfenyl protected 2'-thiol modified nucleoside and FIG. 2b shows the detailed synthesis of a S-tert-butylsulfenyl protected modified adenosine.
Figure 2B:
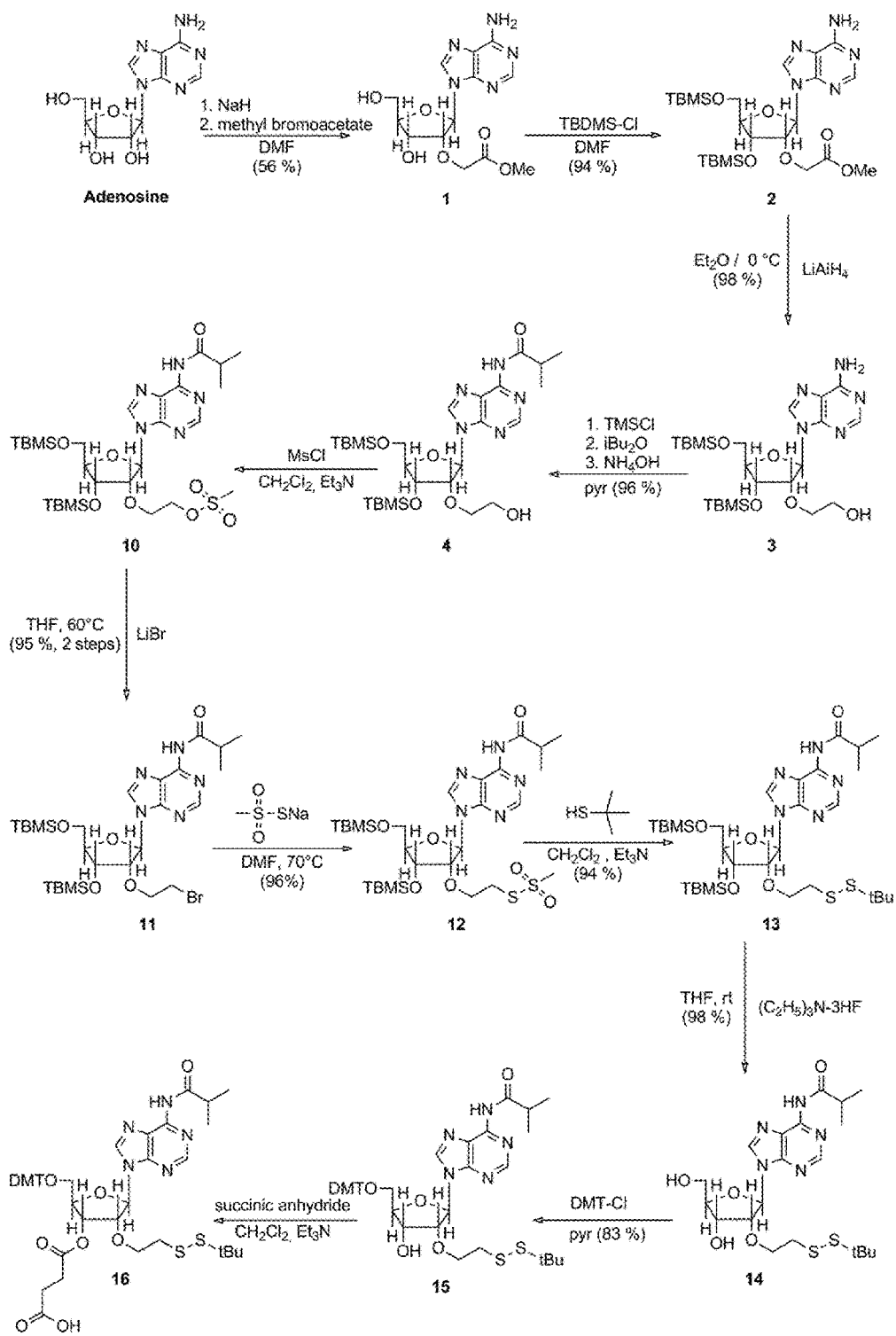

The tbs-protected 2'-thiol modified nucleoside was obtained according to FIG. 2a and FIG. 2b.

Deprotection of tbs can be carried out with phosphorous-containing (preferably TCEP or TBP for their efficiency and ease of use) or sulfur-containing reducing agents (such as dithiothreitol or ethanethiol).

The key compound S5 was accordingly converted in FIG. 2a to the bromide by a mild bromination method after an intermediate mesylation step. The bromide was thereafter converted to the desired activated disulfide terminal by reacting with sodium methane thiosulfonate. Methane thiosulfonate end-group can then be displaced with a free thiol such as 2-methyl-2-propanethiol to afford the stable disulfide compound suitable for on-resin deprotection and capable of withstanding the rigors of phosphoramidite synthesis. Removal of the 3'- and 5'-silyl groups of compounds S7' was quantitatively carried out with triethylamine trihydrofluoride to afford S8'.

The free 5'-hydroxyl group was then protected, e.g with 4,4'-dimethoxytrityl chloride to obtain S9'. After carrying out an esterification at 3, e.g. the corresponding 3'-succinylation S10 can be obtained.

Figure 3A:
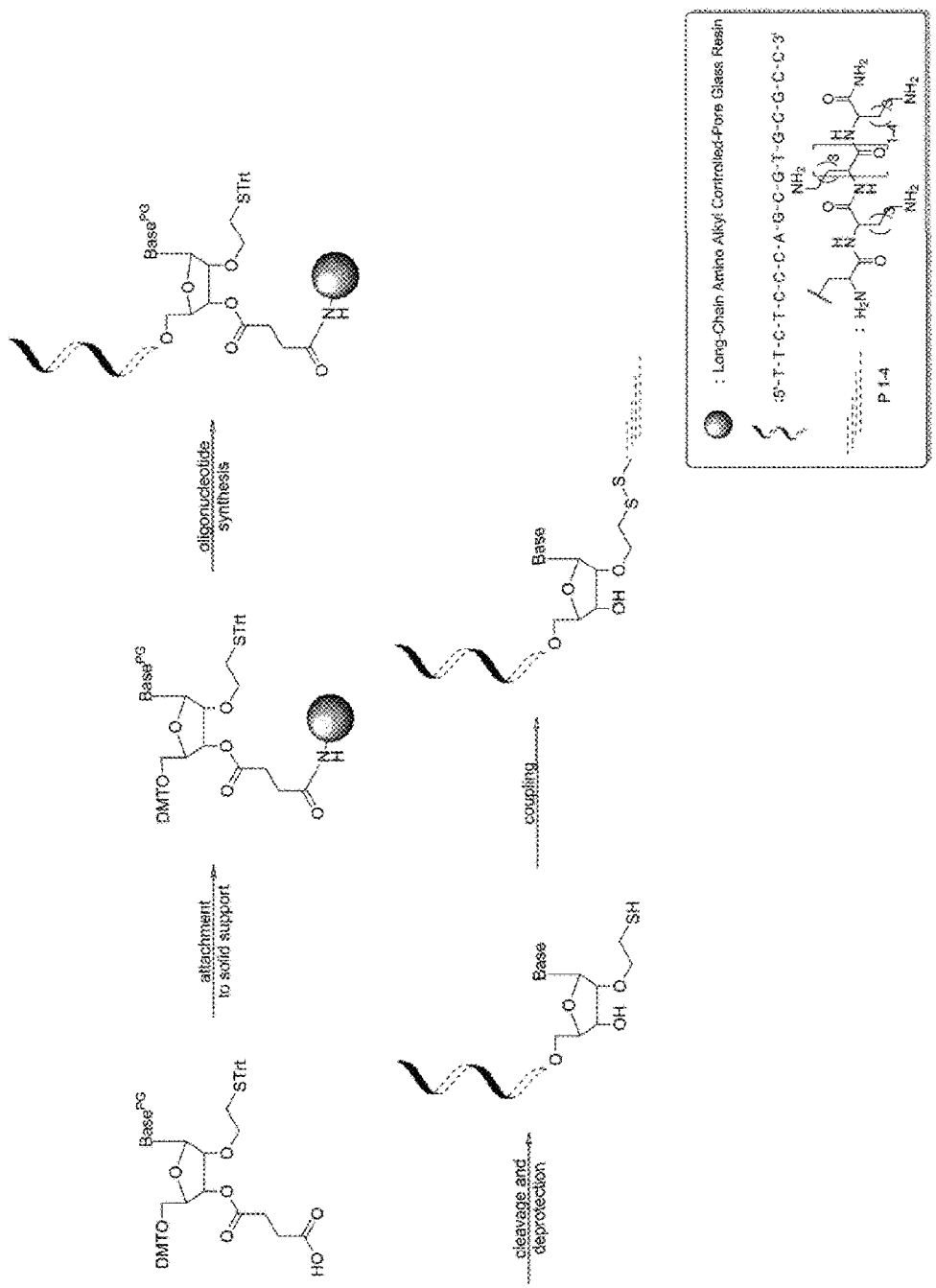
FIG. 3a shows an example of a solution-phase coupling of the oligonucleotide to —CH$_2$—NH$_2$—CO-oligolysine and FIG. 3b shows a detailed example of a solution-phase coupling of the oligonucleotide 5'-TTCTCCCAGCGT-GCGCCA-3' to —CH$_2$—NH$_2$—CO-oligolysine.
Figure 3B:
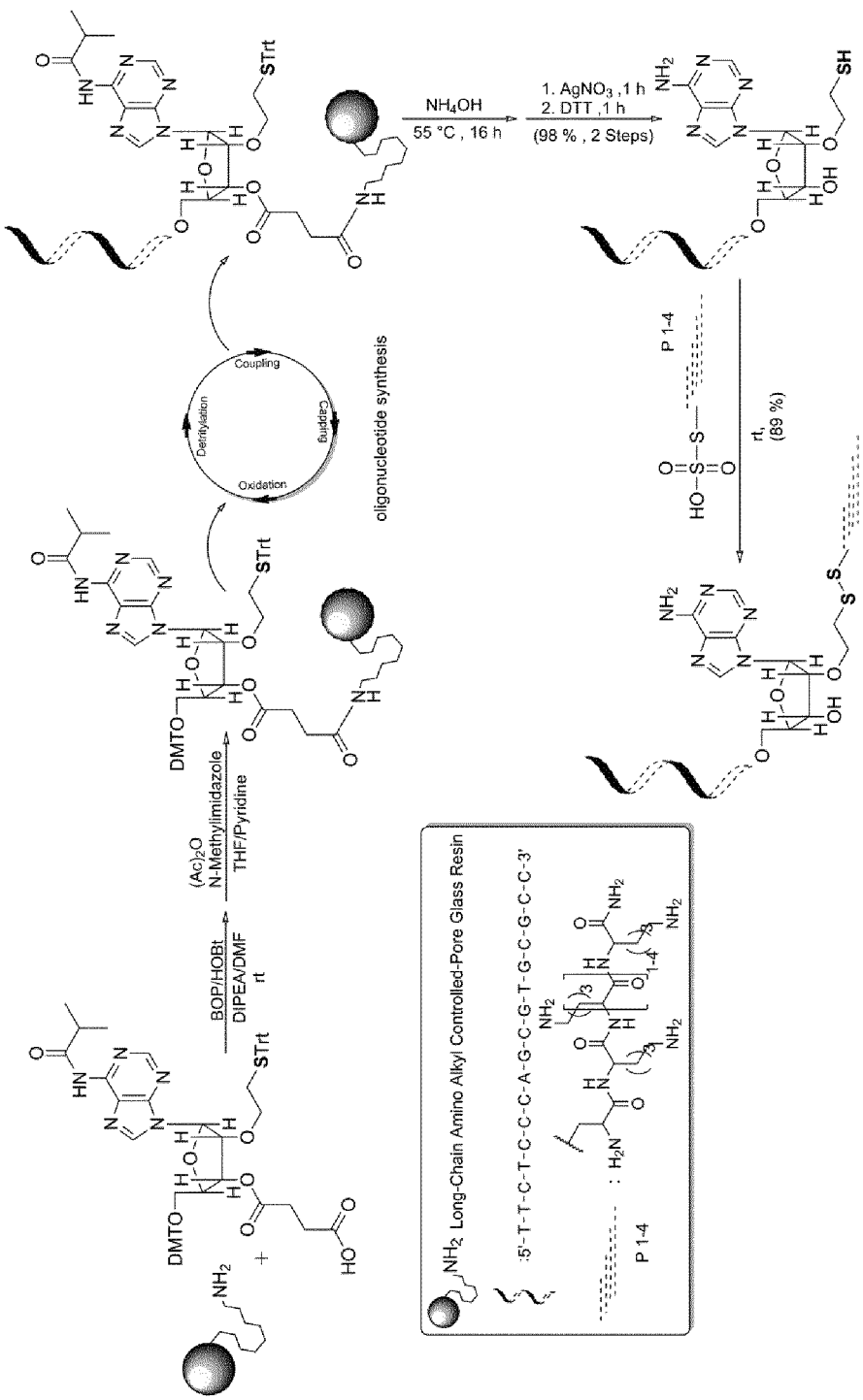

In FIG. 3a and FIG. 3b the amino-functionalized LCAA-CPG (Long Chain Amino Alkyl Controlled Pore Glass) resin was loaded either with S9' or S10 as the first nucleoside of an 17-mer oligonucleotide using (benzotriazol-1-yloxy)tris-(dimethylamino)phosphonium hexafluorophosphate (BOP) activation chemistry. The free-remaining amino groups were then blocked and the loaded resin underwent oligonucleotide synthesis.

The synthesis of oligonucleotide-SS—CH$_2$—NH$_2$—CO-oligolysine conjugates are shown in FIGS. 3a and 3b.

During the synthesis of oligonucleotide-SS—CH$_2$—NH$_2$—CO-oligolysine conjugates a major advantage of post-assembly conjugation is that all peptide side chains and nucleobases are deprotected and thus there is no problem of compatibility of assembly and deprotection chemistries. However, post-assembly joining routes may sometimes lead to inefficient conjugation due to secondary structure or poor solubility of certain peptide components in aqueous solution (a problem which may in some cases be relieved by the addition of denaturants) and usually require cumbersome purification procedures.

The coupling of a 5'- or 3'-thiolated oligonucleotide with a thiol-containing peptide via a disulfide linkage has been reported either by direct oxidation of the two thiols or by preliminary activation of one of the thiol groups with pyridylsulfenyl (Pys) or 3-nitropyridylsulfenyl (Npys) group followed by a nucleophilic substitution reaction. All of these approaches, particularly direct oxidation of the thiol-bearing parts can suffer from intermolecular dimerization side reactions.

A facile coupling method was employed without need for further activation of either of the thiol groups or addition of conjugation enhancers. It was found that it was feasible to avoid the necessity for prior removal of the S-sulfonate protecting group (the protecting group used to protect the thiol group of cysteine in the fmoc/tBu chemistry) from the peptide fragment through its direct reaction with the 2'-thiol-bearing oligonucleotide by a native ligation approach. In this novel conjugation technique, the oligopeptide with S-sulfonate protected cysteine undergoes a rapid displacement reaction with another free thiol functional group thus excluding tedious deprotection/activation steps while ameliorating the risk of dimerization. The free 2'-thiol modified oligonucleotide did not show any tendency towards dimerization in aqueous solutions during the reaction time.

In this series of experiments, oligonucleotide and peptide moieties were assembled separately on their own supports. Both fragments were removed from their supports with the oligonucleotide as S-Tr protected part and the peptide carrying only S-sulfonate protection and purified if necessary.

Figure 4A:
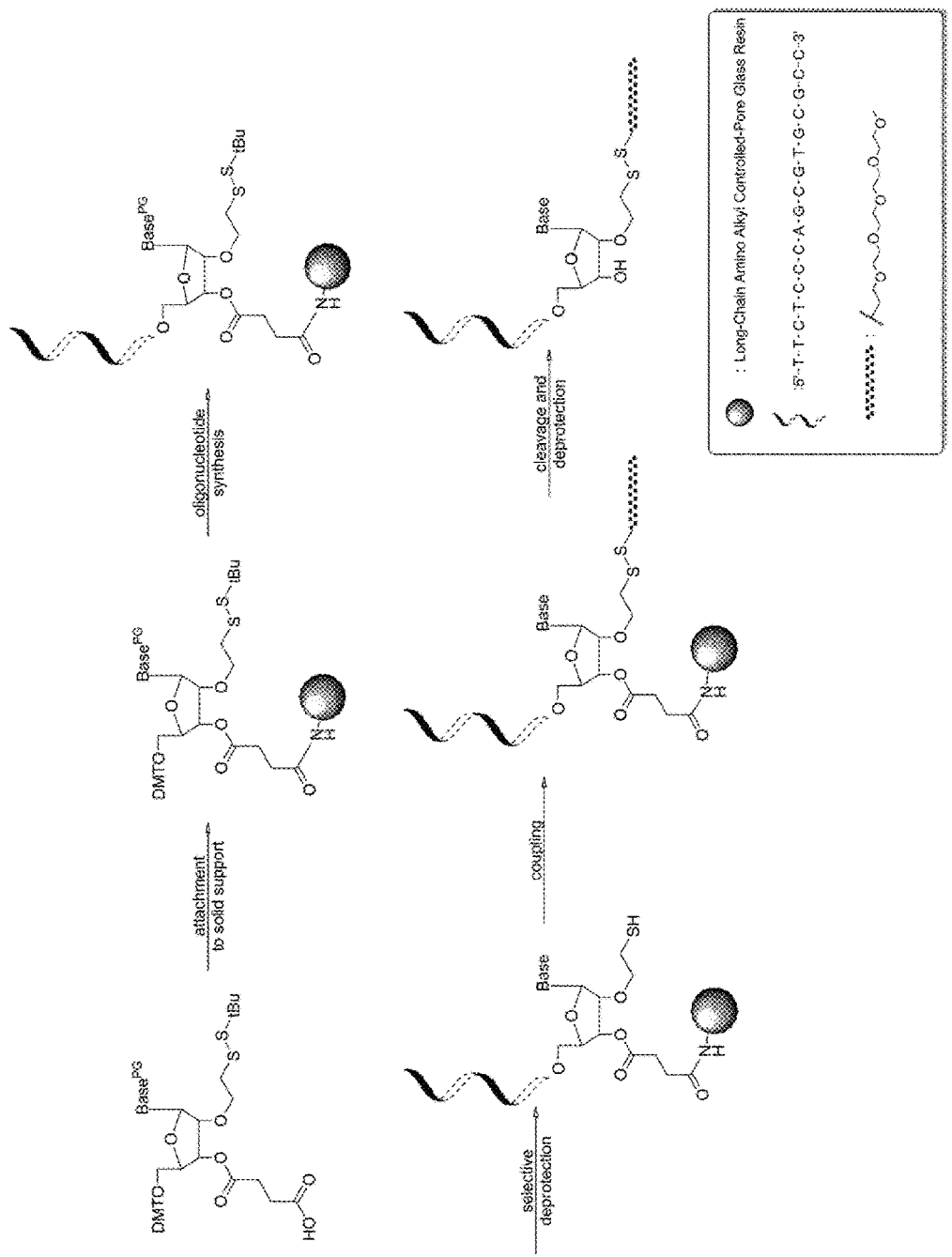
FIG. 4a shows an example of a solid-phase coupling of the oligonucleotide to —(CH$_2$)$_2$-PEG$_5$ and FIG. 4b shows a detailed example of a solid-phase coupling of the oligonucleotide 5'-TTCTCCCAGCGTGCGCCA-3' to —(CH$_2$)$_2$-PEG$_5$.
Figure 4B:
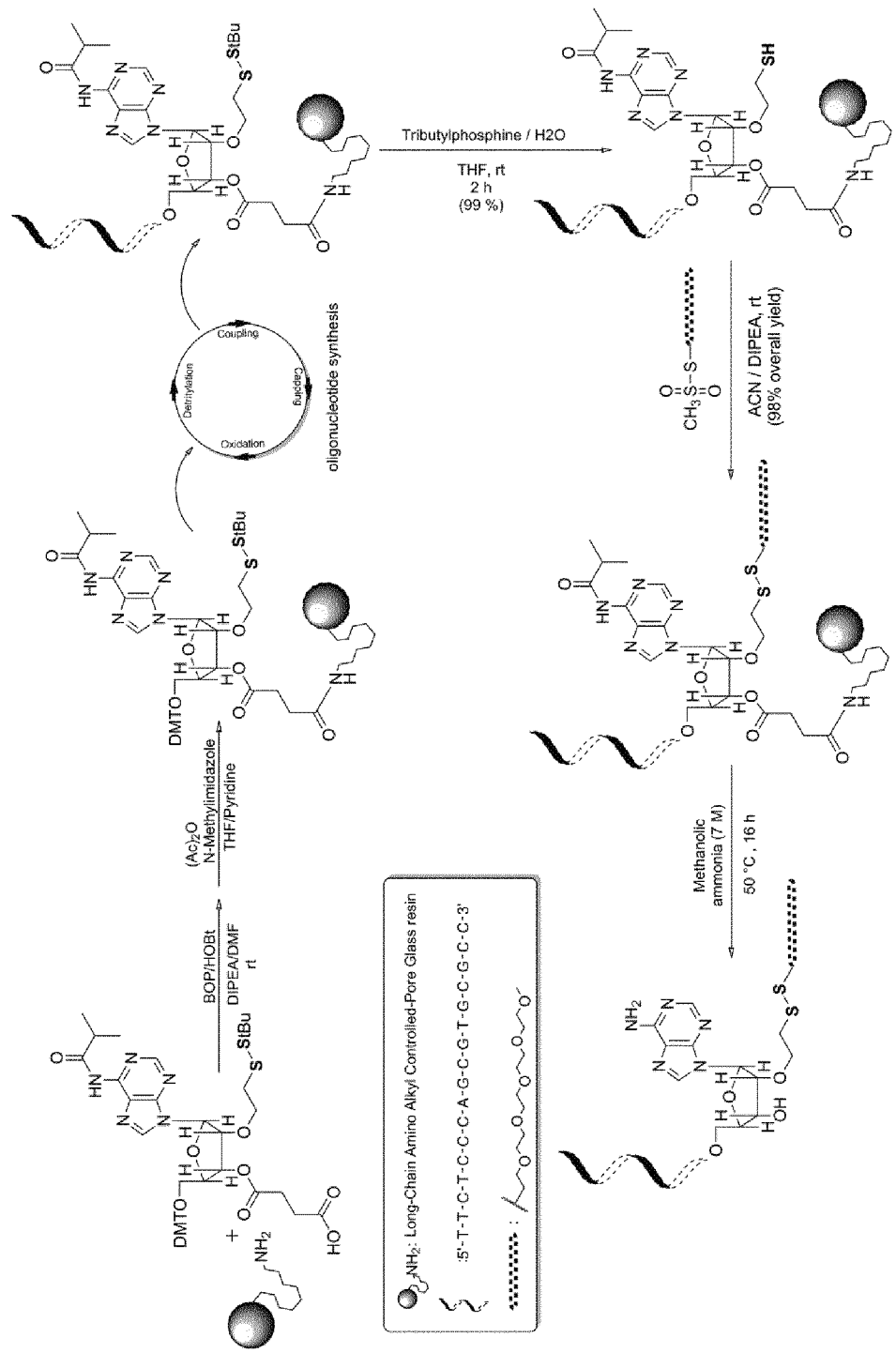

The synthesis of the oligonucleotide-SS—C$_2$H$_4$-oxyethylene conjugate is shown in FIGS. 4a and 4b.

In the solid-phase methodology, the entire conjugate is assembled on a single support, either by conjugation of a prefabricated conjugate group or by assembling the conjugate moiety through a stepwise process prior to or after the oligonucleotide synthesis. The conjugate is obtained following the cleavage from the support, nucleobases deprotection, and purification. The use of a solid support may also help conjugating fragments with different solubility profiles.

In the present invention, oligonucleotide and oxyethylene ligand X including spacer Y were synthesized separately. The oxyethylene fragment including the spacer Y being an ethyl group was purified and used as an S-methanesulfonyl protected thiol.

The conjugates obtained were subsequently screened for their target (Bcl-2) downregulatory effect in 607B melanoma cell line. The zwitterionic conjugates, particularly the ones with 5 and 6 lysine residues showed a great degree of Bcl-2 down-regulation without the use of a transfection enhancer. The PEG-conjugate exerted a significant effect as well, however at slightly higher concentrations than the oligolysine adducts. In another set of experiments, the chemosensitizing effect of the selected conjugates on the antineoplastic activity of cisplatin was explored. The three conjugates tested caused significant chemosensitization of the 607B melanoma cell line toward the cytotoxic effect particularly at lower cisplatin concentrations.

FURTHER ASPECTS OF THE INVENTION

In a further aspect of the invention the invention relates to a pharmaceutical composition comprising the conjugate according to all embodiments of the invention and optionally one or more pharmaceutically acceptable excipients, carriers or diluents.

The conjugates of the invention may also be mixed, encapsulated, conjugated or otherwise associated with other molecules, molecule structures or mixtures of compounds, as for example, liposomes, polymers, receptor targeted molecules, and emulsions for assisting in uptake, distribution and/or absorption.

The pharmaceutical compositions of the present invention comprising the conjugate may be administered in a number of ways depending upon whether local or systemic treatment is desired and upon the area to be treated. Administration may be topical (including ophthalmic and to mucous membranes), pulmonary, e.g., by inhalation of powders or aerosols, including by nebulizer; intratracheal, intranasal, epidermal and transdermal), oral or parenteral.

In another aspect of the invention the invention relates to a pharmaceutical kit comprising (i) a conjugate according to formula (I) a pharmaceutical composition according to the invention and (ii) an antiproliferative drug.

Antiproliferative drugs are known to the skilled person in the art, preferably antiproliferative drugs are used that are already approved by the European Medicines Agency; formerly European Agency for the Evaluation of Medicinal Products or the Food and Drug Administration (FDA) of the United States of America. Those antiproliferative drugs are commonly used in cancer therapy.

The conjugate, pharmaceutical composition or the pharmaceutical kit according to all embodiments of the invention may be used as a medicament or a tool in biomedical research. It can further be used for the treatment of a disease or disorder that can be at least in part alleviated by therapy.

The term medicament is understood as comprising a pharmaceutical drug, also referred to as a medicine or medicinal product defining any chemical substance, or product comprising such, intended for use in the medical diagnosis, cure, treatment, or prevention of disease.

The conjugate, pharmaceutical composition or the pharmaceutical kit according to all embodiments of the invention can also be used as a medicament to promote apoptosis and chemosensitization.

The disease or disorder is selected from the group consisting of bacterial infections, viral infections, cancer, metabolic diseases and immunological disorders, preferably viral infections and cancer and most preferably cancer.

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Due to the pairing properties of the conjugates and oligonucleotides according to the present invention, those compounds may be used as a tool in biomedical research for any purposes known by the skilled person in the art, especially in case that the compounds further comprise detectable probes, dyes and markers that are used for identification purposes, especially in the field of cell metabolism and cell interactions.

The conjugates according to the invention show improved pharmacokinetic properties, e.g. improved efficacy through a cleavable disulfide linker without the need of a transfection agent. Additionally, with respect to the shortcomings of the currently established oligonucleotide conjugate assembly routes, a facile and efficient coupling strategy was found with scale-up compatibility with the potential of being employed in the conjugation of a broad range of vectors to antisense and siRNA oligonucleotides. The functionalization of the 2'-OH-group not only provides a tether for further in-line solid-phase synthesis but also imparts nuclease stability to the conjugates and oligonucleotides according to the invention. The disulfide bonds present in the respective conjugates according to the invention can be cleaved after cellular uptake, preventing detrimental effects of the ligands on hybridization properties of the conjugates and oligonucleotides. Moreover, the conjugates according to the invention show significant biological effects without the addition of a cell penetration enhancer or a pharmaceutical formulation.

In this respect conjugates with improved pharmacokinetic properties were prepared by coupling them at the 2'-position of the conjugate of formula (I) or oligonucleotide of formula (II) through a cleavable disulfide linker. Additionally with respect to the shortcomings of the currently established oligonucleotide conjugate assembly routes, a facile and efficient coupling strategy with scale-up compatibility with the potential of being employed in the conjugation of a broad range of vectors to antisense and siRNA oligonucleotides was established.

Preferably, the present invention is defined as follows:
1. A conjugate of formula I, $$P\text{-}(L\text{-}S\text{—}S\text{—}Y\text{—}X)_n \qquad (I)$$

wherein
P represents a natural, artificial and/or modified oligonucleotide,
L represents a linker group attached to one or more nucleosides at any position within the oligonucleotides sequence;
S represents sulfur;
X represents a ligand;
Y represents a spacer and n is an integer ranging from 1 to the oligonucleotide length of P.

2. An oligonucleotide of formula II,

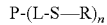     (II)

wherein

P represents a natural, artificial and/or modified oligonucleotide,

L represents a linker group attached to one or more nucleosides at any position within the oligonucleotides sequence, S represents sulfur, R represents either hydrogen or a thiol protecting group, preferably a trityl or a tertiary butyl group, and n is an integer ranging from 1 to the oligonucleotide length of P.

3. A nucleotide or nucleoside according to formula III,

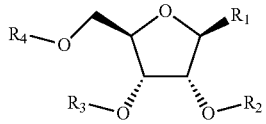     (III)

wherein

R1 represents any N-protected or unprotected, natural or modified nucleobase;

R2 represents a linear, branched, unsubstituted or halogen substituted $C_1$-$C_{10}$ alkyl chain bound to a free thiol group or to an thiol-tertiary butylsulfenyl or thiol-methane sulfonate protected group anywhere in the chain, preferably at the chain end; or a -L-S-trityl group or a -L-S—S-tertiary butyl group, wherein L represents a linker group and S represents sulfur;

R3 represents a succinic ester or a phosphoramidite group or a hydrogen; and

R4 represents independently hydrogen, a protecting group, a monophosphate-P(O)(OH)$_2$, diphosphate —P(O)(OH)—O—P(O)—(OH)$_2$ or triphosphate —P(O)(OH)—O—P(O) (OH)—O—P(O) (OH)$_2$.

4. A conjugate or oligonucleotide according to embodiment 1 or 2, wherein the natural, artificial and/or modified oligonucleotide P comprises natural, artificial and/or modified nucleosides having natural, artificial and/or modified nucleobases, wherein a number of said nucleosides form an oligonucleotide selected from the group consisting of: phosphodiester oligonucleotide (PDOs), phosphorothioate oligonucleotides (PSOs), phosphorodiamidate morpholino oligonucleotides (PMOs), peptide nucleic acids (PNAs), locked nucleic acids (LNAs), ethyl bicyclic nucleic acids (cET BNA), 2'-fluor oligonucleotides, 2'-fluor oligoarabinonucleotides or a combination thereof.

5. A conjugate or oligonucleotide according to embodiment 1 or 2, wherein the linker L is covalently linked via the oxygen atom to the 2' position of the ribose ring of a phosphodiester oligonucleotide, a phosphorothioate oligonucleotide, at the 2' position of the morpholine ring of a phosphorodiamidate morpholino oligonucleotide, or an equivalent position of a peptide nucleic acid.

6. A conjugate, oligonucleotide, nucleotide or nucleoside according to any of the preceding embodiments, wherein the linker L represents a linear alkyl linker of 1 to 10 carbon atoms, or a polyethylene glycol linker of 1 to 20 ethylene glycol units.

7. A conjugate according to any of the preceding embodiments, wherein the ligand X is selected from the group consisting of peptides of 1 to 40 amino acids, preferably polylysine; polyethylene glycols of preferably 2 to 200 ethylene glycol units, preferably a polyethylene glycol having 1 to 20 ethylene glycol units; or polymers with basic charges at neutral or acidic pH and lipophilic compounds.

8. A conjugate according to any of the preceding embodiments, wherein the spacer Y represents a —(CH$_2$)$_m$—NH$_2$—CO— group, wherein m is an integer of 1 to 6 or represents an alkyl group having 1 to 6 carbon atoms or an alkyl group having 1 to 6 carbon atoms.

9. A conjugate according to any of the preceding embodiments, wherein the linker L represents a $C_2$ to $C_{10}$ alkyl linker, the ligand X represents polylysine or polyethylene glycol and the spacer Y represents a —(CH$_2$)$_m$—NH$_2$—CO— group.

10. A conjugate according to any of the preceding embodiments, wherein the linker L represents a polyethylene glycol linker of 1 to 20 ethylene glycol units, the ligand X represents a ligand for receptor-specific interactions and the spacer Y represents an ethyl group.

11. A conjugate or oligonucleotide according to any of the preceding embodiments, wherein the conjugate or oligonucleotide comprises one or more additional linkers L, one or more additional ligands X' and one or more additional spacers Y' at the 2'-O—, 3'-O—, and 5'-O-positions of the oligonucleotide.

12. A conjugate or oligonucleotide according to embodiment 11, wherein the additional linker L' is selected from the group consisting of a linear alkyl linker of 1 to 10 carbon atoms, a polyethylene glycol linker of 1 to 20 ethylene glycol units, the additional ligand X' of the conjugate is a dye, a fluorescence dye, a fluorescence marker or being a ligand X and the additional spacer Y' is a —(CH$_2$)$_m$—NH$_2$—CO— group, wherein m is an integer of 1 to 6 or represents an alkyl group having 1 to 6 carbon atoms or an alkyl group having 1 to 6 carbon atoms.

13. A method for the preparation of a conjugate according to embodiment 1, comprising the following steps of reacting the compound P-(L-S—H)$_n$ having the formula IV with the respective equivalents of a methane thiosulfonate comprising compound HO—SO$_2$—S—Y—X in solution phase or solid phase, wherein P represents a natural, artificial and/or modified oligonucleotide, L represents a linker group attached to one or more nucleosides at any position within the oligonucleotides sequence; S represents sulfur; X represents a ligand; Y represents a spacer and n is an integer ranging from 1 to the oligonucleotide length of P.

14. A method for the preparation of a oligonucleotide P-(L-S—H)$_n$ (IV), wherein the method comprises the step of removing one or more protecting groups from the thiol group of a compound P-(L-S—R)$_n$ (II) with silver nitrate followed by a dithiothreitrol; or tributylphosphine treatment, depending on the protecting group, or alternatively, if R already represents hydrogen in the compound P-(L-S—R), (II) reacting the compound with dithiothreitrol in order to obtain the respective free thiol compound, wherein P represents a natural, artificial and/or modified oligonucleotide, L represents a linker group attached to one or more nucleosides at any position within the oligonucleotides sequence;

S represents sulfur;

n is an integer ranging from 1 to the oligonucleotide length of P and

R represents either hydrogen or a thiol protecting group, preferably a trityl or a tertiary butyl group.

15. A pharmaceutical composition comprising the conjugate according to any of the preceding embodiments and optionally pharmaceutically acceptable excipients, carriers or diluents.

16. A pharmaceutical kit comprising (i) a conjugate according to embodiments 1 to 12 or a pharmaceutical composition according to embodiment 15 and (ii) an antiproliferative drug.

17. Conjugate, pharmaceutical composition or pharmaceutical kit according to any of the preceding embodiments for use as a medicament or a tool in biomedical research.

18. Conjugate, pharmaceutical composition or pharmaceutical kit according to any of the preceding embodiments for the treatment of a disease or disorder that can be at least in part alleviated by therapy.

19. Conjugate of embodiment 18, wherein the disease or disorder is selected from the group consisting of bacterial infections, viral infections, cancer, metabolic diseases and immunological disorders and preferably cancer.

EXAMPLES

As an example a series of embodiments relying on the so called "charge reversal" principle, 4 conjugates were synthesized wherein P (see formula I) represents a phosphodiester oligodeoxynucleotide sequence of $^{5'}$TTC-TCC-CAG-CGT-GCG-CC$\underline{A}^{3'}$ directed against bcl-2 mRNA, conjugated at the 2'-O of the 3'-end, L is an ethyl linker, n is 1 and "X+Y" was selected from the group consisting of
"L-cysteinyl-L-lysyl-L-lysyl-L-lysyl-carboxamide"
"L-cysteinyl-L-lysyl-L-lysyl-L-lysyl-L-lysyl-carboxamide"
"L-cysteinyl-L-lysyl-L-lysyl-L-lysyl-L-lysyl-L-lysyl-carboxamide" and
"L-cysteinyl-L-lysyl-L-lysyl-L-lysyl-L-lysyl-L-lysyl-L-lysyl-carboxamide".

In this embodiment the conjugates of the invention were synthesized according to the coupling technique as shown in FIG. 3b.

P-ethyl-S-Tr was deprotected by treatment with aqueous silver nitrate (FIG. 3b) followed by regeneration of the thiol functional group by addition of excess dithiothreitol (DTT). Hamm et al. reported that Ag$^+$/DTT-based deprotection strategy resulted in significant loss of oligonucleotide in the precipitate, however, in the examples of the present invention an almost quantitative two-step conversion in a more dilute reaction mixture was achieved (concentrations up to 1 µM).

Upon treatment with silver nitrate solution and subsequent regeneration, a free thiol group was generated. As a first trial, the conjugation in aqueous Tris buffer solution was evaluated. The oligonucleotide was mixed in each case with the corresponding oligolysine fragment. For the conjugation of the hexalysine fragment, a denaturing agent (urea) had to be added to the buffer to ameliorate the aggregation tendency of the species and to improve the inadequate solubility encountered. The reaction progress was monitored by reversed-phase HPLC.

Example of Conjugation:

To a solution of the oligonucleotide (20 nmol) in 1500 µL of doubly-distilled water was added silver nitrate (600 nmol; 1000 µL of a 6 mM aqueous solution). The solution was shaken gently for 1 h followed by the addition of DTT (8 µL, aqueous 0.1 M in 0.5 tris-HCl buffer, pH 8.0). The reaction mixture was then incubated for another 1 h at room temperature and centrifuged (15,000 g, 15 min at 20° C.). The supernatant was concentrated to a small volume and the deprotected oligonucleotide was precipitated from isopropanol (3 volumes).

The suspension was immediately centrifuged (15,000 g, 15 min at 4° C.) and the pellet was dried. The overall efficiency of the process (deprotection/regeneration/isolation) was assessed by HPL chromatography. Following HPLC analysis, the products (showing at least 75% purity as integrated from the HPLC traces) were analyzed by high-resolution mass spectrometry.

The deprotected oligonucleotide was taken up in 150 µL of tris-HCl/EDTA/NaCl (50 mM/1 mM/100 mM, pH 7.5) buffer for the couplings with —CH$_2$-(PEG)$_1$OMe to —CH$_2$-(PEG)$_3$OMe and in 300 µL of tris-HCl/EDTA/NaCl/urea (50 mM/1 mM/100 mM/7 M; pH 7.5) buffer for —CH$_2$-(PEG)$_4$OMe coupling. The corresponding oligopeptide was subsequently added (4 equiv) and the reaction mixture was incubated at 25° C. for 2 h. The conjugation efficiency was monitored and optimized by HPLC. After completion of the reaction, the mixture was passed through a column of Sephadex™ G-25 to remove the salts and oligopeptide excess.

In another embodiment relying on the "stealth" strategy, one conjugate was synthesized with P being a phosphodiester oligodeoxynucleotide sequence of $^{5'}$TC-TCC-CAG-CGT-GCG-CC$\underline{A}^{3'}$ directed against bcl-2 mRNA, conjugated at the 2'-O of the 3'-end, L an ethyl linker, and n=1. "X+Y" is the structural unit "ethyl-(OEt)$_4$OMe" of the following compound.

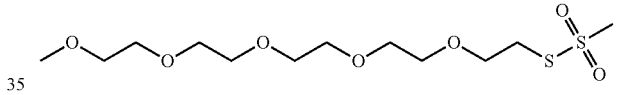

In this embodiment conjugate synthesis was performed according to the following procedure:

The initially incorporated (at the 3'-end as the first building block) 2'-thiol tethered nucleoside was deprotected with tributylphosphine before/after oligonucleotide assembly and prior to final deprotection/cleavage step. Addition of an excess of the corresponding fragment carrying the thiol complementary part resulted in complete conversion of the starting material. The disulfide formation reaction was optimized using the colorimetric Ellman's test and was assessed to be complete after 4 hours.

In this synthesis, the regular ammonium hydroxide deprotection/cleavage step was replaced with a methanolic ammonia (7N) deprotection/cleavage profile. The purity of the resulting conjugate was determined by HPLC.

Example of Conjugation:

The loaded resin (10 mg) was slurried in tetrahydrofuran (200 µL) followed by addition of tri-N-butylphosphine (4 equiv). After 5 min, 1 µL doubly-distilled water was added and the reaction mixture was agitated gently for 2 h at 25° C. Subsequently, the resin was filtered off and washed three times with tetrahydrofuran, methanol and dichloromethane and dried in an evacuated exsiccator overnight. The assessment of deprotection and the optimization of the reaction were carried out employing the Ellman test.

The resin from the previous step (deprotection) was suspended in a mixture of the oxyethylene ligand (3 equiv) in 200 µL anhydrous acetonitrile followed by the addition of DIPEA (6 equiv). The reaction mixture was agitated gently at room temperature for 4 h and the resin was filtered off, washed three times with acetonitrile and dichloromethane and air-dried. Optimization of reaction conditions and reaction time was carried out by performing the Ellman test.

In another embodiment, a modified nucleoside of the formula (II) was synthesized

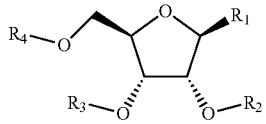

wherein R1 is an N-ibutyryl protected adenine, R2 is a 2-bromoethyl alkyl chain, R3 and R4 are tertbutylmethylsilyl groups.

Synthesis of Compound 11

A stirred solution of the precursor compound, with R2 being the 2-hydroxyethyl (2.10 g, 3.44 mmol) in 11 mL anhydrous dichloromethane and 4 mL triethylamine was cooled to 0° C. in an argon atmosphere. Methanesulfonyl chloride (0.43 g, 3.80 mmol) was diluted in 4 mL dichloromethane and added dropwise via a syringe. The reaction mixture was stirred at room temperature for 2 h and subsequently evaporated to dryness. The orange oily residue was taken up in ethyl acetate and washed with 1 M-sodium bicarbonate solution, water and brine and dried over sodium sulfate followed by evaporation of the solvent under vacuum.

The residue was then dissolved in 15 mL anhydrous tetrahydrofuran and mixed with a solution of ultra-dry lithium bromide (0.90 g, 10.32 mmol) in anhydrous tetrahydrofuran in an argon atmosphere. After heating the reaction mixture at 60° C. for 6 h, thin-layer chromatography showed complete conversion of the starting material. Afterwards, the solvent was removed and the pale yellow residue was redissolved in ethyl acetate.

The organic phase was washed water and brine, dried over sodium sulfate and chromatographed on a silica gel column eluted with a gradient of 0-70% tert-butyl methyl ether in petroleum ether. The corresponding fractions were pooled and evaporated under vacuum to produce 2.11 g (91%) of a pale yellow powder as the product.

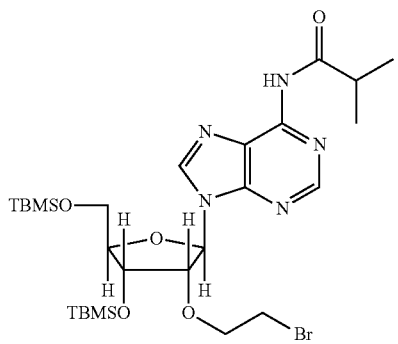

$R_f$ 0.35 (1:20 MeOH/CH$_2$Cl$_2$)

$^1$H NMR (500 MHz, CDCl$_3$): δ=8.72 (s, 1H, H-2), 8.60 (br s, 1H, NH), 8.36 (s, 1H, H-8), 6.19 (d, J=3.8 Hz, 1H, H-1'), 4.51 (dd, J=5.35 and 3.8, 1H, H-3'), 4.41 (dd, J=4.9, 3.8 Hz, 1H, H-2'), 4.14 (dt, J=5.7, 2.8 Hz, 1H, H-4'), 4.00 (dd, J=11.7, 3.5 Hz, 1H, H-5'1), 3.97-3.87 (m, 2H, OCH$_2$), 3.78 (dd, J=11.7, 2.9 Hz, 1H, H-5'/2), 3.44 (t, J=6.3 Hz, 1H, BrCH$_2$), 3.19 (septet, J=6.0 Hz, 1H, i-prCH), 1.30 (d, J=6.9 Hz, 6H, i-prCH$_3$), 0.92 (s, 18H, tert-BuCH$_3$), 0.11 (s, 3H, SiCH$_3$), 0.10 (s, 9H, SiCH$_3$).

$^{13}$C NMR (125 MHz, CDCl$_3$): δ=176.00 (CON), 152.61 (C-2), 150.82 (C-4), 149.26 (C-6), 141.54 (C-8), 122.47 (C-5), 87.15 (C-1'), 84.99 (C-4'), 82.40 (C-2'), 70.71 (2'-OCH$_2$), 69.87 (C-3'), 61.64 (C-5'), 36.17 (i-prCH), 29.83 (BrCH$_2$), 25.99 (tert-BuCH$_3$), 25.70 (tert-BuCH$_3$), 19.19 (i-prCH$_3$), 18.44 (tert-BuC), 18.09 (tert-BuC), −4.86 (SiCH$_3$), −5.42 (SiCH$_3$).

ESI-HRMS m/z [M+H]$^+$: calculated for C$_{28}$H$_{51}$BrN$_5$O$_5$Si$_2$ 672.2606. found 672.2632.

In another embodiment a modified nucleoside 12 was synthesized wherein R1 is an N-ibutyryl protected adenine, R2 is a 2-(S-methanesulfonyl)ethyl chain, R3 and R4 are tertbutylmethylsilyl groups.

Synthesis Thereof:

To a solution of the compound with R1 2-bromoethyl (600 mg, 0.89 mmol) in 15 mL anhydrous dimethylformamide was added sodium methanethiosulfonate (0.131 g, 0.98 mmol) in an argon atmosphere. The reaction mixture was heated at 70° C. until thin-layer chromatography revealed completion of the reaction (16 h).

The solvent was then removed under vacuum and the residue was taken up in ethyl acetate, washed with water and brine and dried over sodium sulfate. The organic phase was evaporated to obtain 0.60 g (96%) of pale yellow crystals as the desired product that was used without further purification.

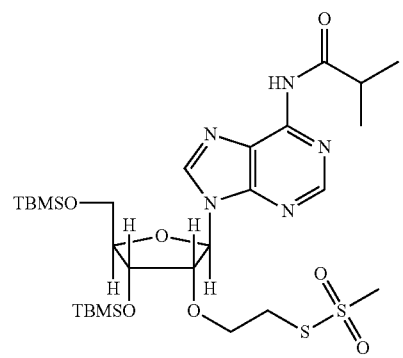

$R_f$ 0.29 (tert-butyl methyl ether)

$^1$H NMR (500 MHz, CDCl$_3$): δ=8.70 (s, 1H, H-2), 8.53 (br s, 1H, NH), 8.37 (s, 1H, H-8), 6.18 (d, J=3.2 Hz, 1H, H-1'), 4.52 (t, J=5.1 Hz, 1H, H-3'), 4.32 (dd, J=3.2, 2.9 Hz, 1H, H-2'), 4.14 (dt, J=2.9, 2.5 Hz, 1H, H-4'), 4.01 (dd, J=11.7, 2.8 Hz, 1H, H-5'/1), 3.95 (t, J=5.7 Hz, 2H, OCH$_2$), 3.78 (dd, J=11.7, 2.8 Hz, 1H, H-5'/2), 3.37 (dd, J=9.5, 5.4 Hz, 2H, SCH$_2$), 3.34 (s, 3H, —SO$_2$CH$_3$), 3.21 (septet, J=6.5 Hz, 1H, i-prCH), 1.31 (d, J=7.0 Hz, 6H, i-prCH$_3$), 0.93 (s, 9H, tert-BuCH$_3$), 0.92 (s, 9H, tert-BuCH$_3$), 0.11 (s, 12H, SiCH$_3$).

$^{13}$C NMR (125 MHz, CDCl$_3$): δ=175.93 (CON), 152.58 (C-2), 150.69 (C-4), 149.30 (C-6), 141.31 (C-8), 122.43 (C-5), 87.01 (C-1'), 84.83 (C-4'), 82.82 (C-2'), 69.58 (C-3'), 69.46 (2'-OCH$_2$), 61.50 (C-5'), 50.58 (—SO$_2$CH$_3$), 36.20 (SCH$_2$), 36.18 (i-prCH), 25.99 (tert-BuCH$_3$), 25.71 (tert-BuCH$_3$), 19.18 (i-prCH$_3$), 18.45 (tert-BuC), 18.07 (tert-BuC), −4.53 (SiCH$_3$), −5.42 (SiCH$_3$).

ESI-HRMS m/z [M+H]$^+$: calculated for C$_{29}$H$_{54}$N$_5$O$_7$S$_2$Si$_2$ 704.2998. found 704.2935.

In another embodiment a modified nucleoside 13 was synthesized wherein R1 is an N-ibutyryl protected adenine, R2 is a 2-(S-tertbutylsulfenyl)ethyl chain, R3 and R4 are tertbutylmethylsilyl groups.

Synthesis Thereof:

2-Methyl-2-propanethiol (0.092 g, 1.02 mmol) was added dropwise to a cooled (ice bath) solution of the modified nucleoside with R2 2-(S-methanesulfonyl)ethyl chain (0.60 g, 0.85 mmol) in 5 mL dichloromethane containing 2 equiv of (0.24 mL) triethylamine. After stirring for 6 h (TLC) at room temperature, the solvents were removed under vacuum. The residue was taken up in ethyl acetate and washed with water and brine followed by drying over natrium sulfate. The solution was thereafter evaporated and the residue was chromatographed on a silica gel column. The title compound was eluted with a 0-50% gradient of tert-butyl methyl ether in petroleum ether to obtain 0.57 g (94%) of a white powder.

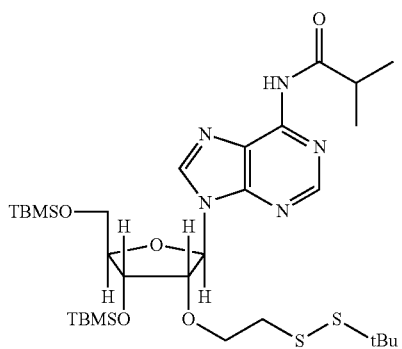

13

$R_f$ 0.35 (1:1 tert-butyl methyl ether/petroleum ether)

$^1$H NMR (500 MHz, CDCl$_3$): δ=8.72 (s, 1H, H-2), 8.51 (br s, 1H, NH), 8.34 (s, 1H, H-8), 6.17 (d, J=4.1 Hz, 1H, H-1'), 4.50 (dd, J=5.1, 4.7 Hz, 1H, H-3'), 4.39 (t, J=4.4 Hz, 1H, H-2'), 4.13 (ddd, J=7.9, 6.9, 3.2 Hz, 1H, H-4'), 4.00 (dd, J=11.4, 3.8 Hz, 1H, H-5'/1), 3.84-3.76 (m, 3H, OCH$_2$ and H-5'/2), 3.21 (septet, J=6.5 Hz, 1H, i-prCH), 3.37 (dd, J=7.0, 6.6 Hz, 2H, SCH$_2$), 1.31 (d, J=6.6 Hz, 6H, i-prCH$_3$), 1.28 (s, 9H, S-tertBuCH$_3$), 0.93 (s, 9H, Si-tert-BuCH$_3$), 0.92 (s, 9H, Si-tert-BuCH$_3$), 0.11 (s, 12H, SiCH$_3$), 0.12 (s, 3H, SiCH$_3$), 0.10 (s, 9H, SiCH$_3$).

$^{13}$C NMR (125 MHz, CDCl$_3$): δ=175.92 (CON), 152.59 (C-2), 150.90 (C-4), 149.20 (C-6), 141.59 (C-8), 122.46 (C-5), 87.10 (C-1'), 84.20 (C-4'), 82.22 (C-2'), 69.93 (C-3'), 69.52 (2'-OCH$_2$), 61.83 (C-5'), 47.87 (S-tertBuC), 39.68 (SCH$_2$), 36.17 (i-prCH), 29.76 (S-tertBuCH$_3$), 25.99 (Si-tert-BuCH$_3$), 25.74 (Si-tert-BuCH$_3$), 19.19 (i-prCH$_3$), 18.44 (Si-tert-BuC), 18.12 (Si-tert-BuC), −4.54 (SiCH$_3$), −4.83 (SiCH$_3$), −5.40 (SiCH$_3$), −5.42 (SiCH$_3$).

ESI-HRMS m/z [M+H]+: calculated for C$_{32}$H$_{60}$N$_5$O$_5$S$_2$Si$_2$ 714.3569. found 714.3601.

In another embodiment a modified nucleoside 14 was synthesized wherein R1 is an N-ibutyryl protected adenine, R2 is a 2-(S-tertbutylsulfenyl)ethyl chain, each R3 and R4 is independently a hydrogen atom.

Synthesis Thereof:

To a solution of a modified nucleoside (formula II) with R2 (0.25 g, 0.35 mmol) in 2 mL tetrahydrofuran was added triethylamine trihydrofluoride 97% (0.23 g, 1.40 mmol) dropwise and stirred at room temperature for 4 h until thin-layer chromatography showed complete deprotection of the starting material.

The solvent was then evaporated and the residue was taken up in ethyl acetate, washed with water and brine and dried over sodium sulfate. The organic phase was removed to produce 0.170 g (98%) of the desired product as a pale yellow foam which was used without further purification.

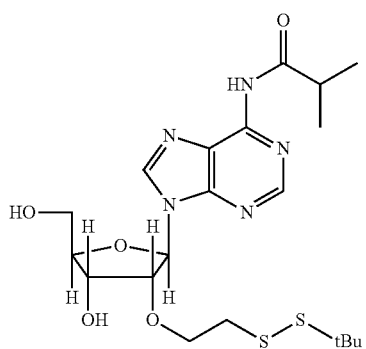

14

$R_f$ 0.31 (1:15 MeOH/CH$_2$/Cl$_2$)

$^1$H NMR (500 MHz, CDCl$_3$): δ=8.70 (s, 1H, H-2), 8.61 (br s, 1H, NH), 8.05 (s, 1H, H-8), 6.13 (d, J=11.7 Hz, 1H, OH-5'), 5.94 (d, J=7.6 Hz, 1H, H-1'), 4.83 (dd, J=7.6, 4.4 Hz, 1H, H-2'), 4.58 (d, J=4.4, 1H, H-3'), 4.38 (s, 1H, H-4'), 3.97 (d, J=13.00 Hz, 1H, H-5'/1), 3.79 (d, J=12.00 Hz, 1H, H-5'/2), 3.77-3.67 (m, 2H, OCH$_2$), 3.24 (septet, J=6.00 Hz, 1H, i-prCH), 3.14 (s, 1H, OH-5'), 2.76-2.68 (m, 2H, SCH$_2$), 1.31 (d, J=7.00 Hz, 6H, i-prCH$_3$), 1.28 (s, 9H, S-tertBuCH$_3$).

$^{13}$C NMR (125 MHz, CDCl$_3$): δ=175.98 (CON), 152.04 (C-2), 150.08 (C-4), 150.05 (C-6), 143.08 (C-8), 123.72 (C-5), 89.44 (C-1'), 88.04 (C-4'), 81.29 (C-2'), 70.94 (C-3'), 68.71 (2'-OCH$_2$), 63.25 (C-5'), 48.25 (S-tertBuC), 39.83 (SCH$_2$), 36.19 (i-prCH), 29.79 (S-tertBuCH$_3$), 19.16 (i-prCH$_3$), 19.10 (i-prCH$_3$).

ESI-HRMS m/z [M+H]+: calculated for C$_{20}$H$_{32}$N$_5$O$_5$S$_2$ 486.1839. found 486.1843.

In another embodiment a modified nucleoside 15 was synthesized wherein R1 is an N-ibutyryl protected adenine, R2 is a 2-(S-tertbutylsulfenyl)ethyl chain, R3 is a hydrogen atom and R4 is a 4,4'-dimethoxytrityl protecting group.

Synthesis Thereof:

4,4'-Dimethoxytrityl chloride (0.058 g, 0.17 mmol) was added to a cooled solution of the precursor compound (0.075 g, 0.15 mmol) in 1 mL of anhydrous dichloromethane containing 3 equiv triethylamine (0.065 mL). The reaction mixture was allowed to warm up to room temperature and stirred for 16 h until thin-layer chromatography showed completion of the reaction.

After quenching the reaction for 0.5 h in the presence of 0.5 mL of methanol, the solvents were removed under vacuum and the residue was redissolved in ethyl acetate, washed with saturated sodium bicarbonate solution, water, brine and dried over natrium sulfate. The organic phase was then evaporated and the resulting yellow foam was recrystallized from tert-butyl methyl ether/n-hexane to give 0.098 g (83%) of the title compound as a pale yellow foam.

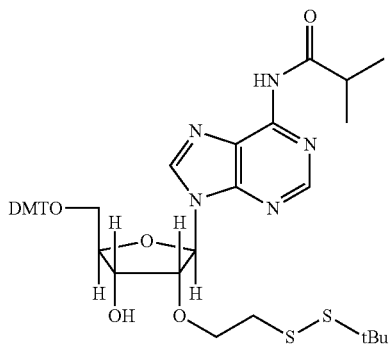

15

$R_f$ 0.27 (1:40 MeOH/CH$_2$/Cl$_2$)

$^1$H NMR (500 MHz, CDCl$_3$): δ=8.65 (s, 1H, H-2), 8.46 (br s, 1H, NH), 8.20 (s, 1H, H-8), 7.43 (d, J=7.60 Hz, 2H, Ph-2, 6), 7.32 (dd, J=8.9, 1.6 Hz, 4H, Ar-2, 6), 7.29-7.22 (m, 3H, Ph-3, 4, 5), 6.81 (d, J=8.60 Hz, 4H, Ar-3, 5), 6.18 (d, J=3.8 Hz, 1H, H-1'), 4.63 (dd, J=4.7, 4.1 Hz, 1H, H-2'), 4.52 (dd, J=11.1, 5.4, 1H, H-3'), 4.24 (dt, J=8.5, 4.1 Hz, 1H, H-4'), 4.05 (ddd, J=10.4, 7.3, 5.4 Hz, 1H, OCH$_2$/1), 3.89-3.87 (m, 1H, OCH$_2$/1), 3.79 (s, 3H, OMe), 3.53 (dd, J=10.70, 3.2 Hz, 1H, H-5'/1), 3.43 (dd, J=10.8, 3.20 Hz, 1H, H-5'/2), 3.17 (septet, J=6.81 Hz, 1H, i-prCH), 2.90-2.86 (m, 2H, SCH$_2$), 1.32 (d, J=7.00 Hz, 6H, i-prCH$_3$), 1.28 (s, 9H, S-tertBuCH$_3$).

$^{13}$C NMR (125 MHz, CDCl$_3$): δ=175.82 (CON), 158.55 (Ar-4), 152.63 (C-2), 150.89 (C-4), 149.26 (C-6), 144.43 (Ph-1), 141.38 (C-8), 135.64 (Ar-1), 135.56 (Ar-1), 130.07 (Ar-2, 6), 128.16 (Ph-2, 6), 127.90 (Ph-3, 5), 126.97 (Ph-4), 122.58 (C-5), 113.19 (Ar-3, 5), 87.10 (C-1'), 86.64 (trityl-C), 84.05 (C-4'), 81.94 (C-2'), 69.82 (C-3'), 69.33 (2'-OCH$_2$), 62.82 (C-5'), 55.23 (OMe), 48.17 (S-tertBuC), 39.92 (SCH$_2$), 36.24 (i-prCH), 29.83 (S-tertBuCH$_3$), 19.19 (i-prCH$_3$).

ESI-HRMS m/z [M+H]$^+$: calculated for C$_{41}$H$_{50}$N$_5$O$_7$S$_2$ 788.3146. found 788.3097.

In another embodiment a modified nucleoside 16 was synthesized wherein R1 is an N-ibutyryl protected adenine, R2 is a 2-(S-tertbutylsulfenyl)ethyl chain, R3 is a succinic ester and R4 is a 4,4'-dimethoxytrityl protecting group.

Synthesis Thereof:

The precursor compound (0.060 g, 0.076 mmol) was dissolved in 2 mL anhydrous dichloromethane containing 3 equiv (0.032 mL) triethylamine in an argon atmosphere. The reaction mixture was cooled in an ice bath before succinic anhydride (0.015 g, 0.15 mmol) was added.

The reaction mixture was stirred for 1 h at 0° C. and allowed to come slowly to room temperature. After 2 h, thin-layer chromatography revealed complete conversion of the starting material. Solvents were removed under vacuum, the residue redissolved in ethyl acetate and washed with saturated bicarbonate solution, water, brine and dried over sodium sulfate. The solution was then evaporated to dryness under vacuum and the residue was recrystallized from tert-butyl methyl ether/n-hexane to produce 0.066 g (98%) of the title compound as a pale yellow foam.

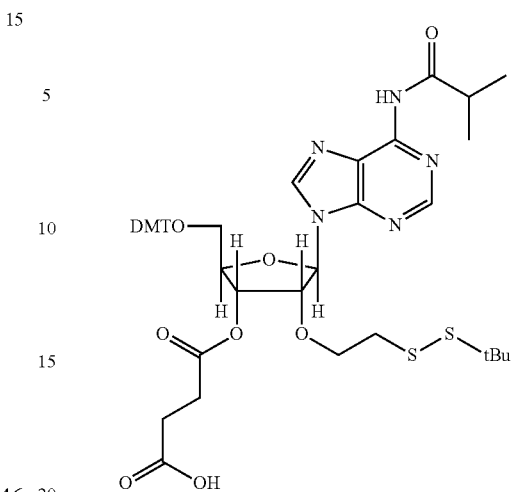

16

$R_f$ 0.17 (1:20 MeOH/CH$_2$/Cl$_2$)

$^1$H NMR (500 MHz, CDCl$_3$): δ=8.90 (br s, 1H, NH), 8.63 (s, 1H, H-2), 8.16 (s, 1H, H-8), 7.40 (d, J=7.60 Hz, 2H, Ph-2, 6), 7.30 (d, J=8.8 Hz, 4H, Ar-2, 6), 7.27-7.16 (m, 3H, Ph-3, 4, 5), 6.81 (d, J=7.60 Hz, 4H, Ar-3, 5), 6.12 (d, J=6 Hz, 1H, H-1'), 5.47 (dd, J=4.8, 3.5, 1H, H-3'), 4.93 (t, J=5.7 Hz, 1H, H-2'), 4.36 (dt, J=6.9, 3.5 Hz, 1H, H-4'), 3.78 (s, 3H, OMe), 3.84-3.67 (m, 2H, OCH$_2$), 3.53 (dd, J=10.7, 3.5 Hz, 1H, H-5'/1), 3.41 (dd, J=10.8, 3.8 Hz, 1H, H-5'/2), 3.14 (septet, J=6.7 Hz, 1H, i-prCH), 2.81-2.66 (m, 6H, succin-CH$_2$ and SCH$_2$), 1.299 (d, J=7.0 Hz, 3H, i-prCH$_3$), 1.295 (d, J=6.9 Hz, 3H, i-prCH$_3$), 1.23 (s, 9H, S-tertBuCH$_3$).

$^{13}$C NMR (125 MHz, CDCl$_3$): δ=175.99 (CON), 171.27 (COO), 158.61 (Ar-4), 152.66 (C-2), 151.28 (C-4), 149.48 (C-6), 144.24 (Ph-1), 141.17 (C-8), 135.39 (Ar-1), 135.36 (Ar-1), 130.07 (Ar-2, 6), 128.13 (Ph-2, 6), 127.96 (Ph-3, 5), 127.05 (Ph-4), 122.38 (C-5), 113.25 (Ar-3, 5), 86.90 (trityl-C), 86.68 (C-1'), 82.20 (C-4'), 80.09 (C-2'), 71.53 (C-3'), 69.73 (2'-OCH$_2$), 62.86 (C-5'), 55.23 (OMe), 48.89 (S-tertBuC), 39.75 (SCH$_2$), 36.16 (i-prCH), 29.75 (S-tertBuCH$_3$), 29.12 (succin-CH$_2$), 19.19 (i-prCH$_3$).

ESI-HRMS m/z [M+Na]$^+$: calculated for C$_{45}$H$_{53}$N$_5$NaO$_{10}$S$_2$ 910.3126. found 910.3207.

Figure 14:
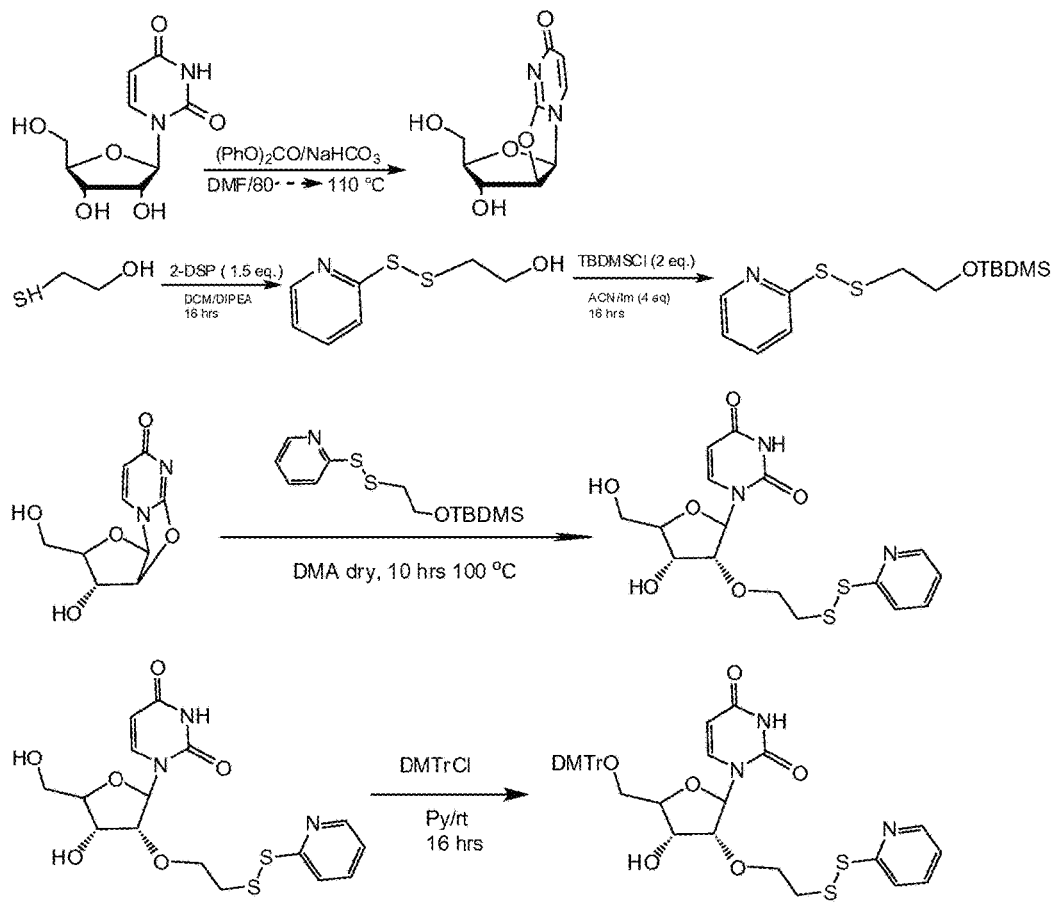
FIG. 14 shows an example of a preparation of a 2-oxo-pyrimidine nucleoside 2' conjugate.

Example of a preparation of 2-oxo-pyrimidine nucleoside 2' conjugates (FIG. 14):

The example describes the formation of a 2-2'-anhydropyrimidine nucleoside, the formation of the side chain, which is subsequently conjugated to the 2' position of the ribose of the 2-oxo-pyrimidine nucleoside, and the protection of the 5' position of the ribose of the 2-oxo-pyrimidine nucleoside.

2-2'-anhydropyrimidine nucleoside formation

Uridine (10 g, 41 mmol) and diphenylcarbonate (10 g, 47 mmol) were dissolved in 20 mL anhydrous dimethylformamide and the mixture was heated at 80° C. until a clear solution ensued. Afterwards, sodium bicarbonate (250 mg) was added and the reaction mixture was heated to 110° C. for 3 hours. After cooling down, the slurry was filtered. The solid was then recrystallized from methanol to give white prisms in 95% yield.

$^1$H NMR (500 MHz, DMSO-d$_6$): δ 7.84 (d, J=10.0 Hz, 1H), 6.31 (d, J=5.0 Hz, 1H), 5.89 (s, 1H, OH-3'), 5.84 (d, J=10.0 Hz, 1H), 5.20 (d, J=5.0 Hz, 1H), 4.99 (s, 1H, OH-5'), 4.38 (s, 1H), 4.08-4.06 (m, 1H), 3.29-3.28 (m, 1H), 3.19 (m, 1H).

¹³C NMR (125 MHz, DMSO-d$_6$): δ 171.20 (C-4), 159.82 (C-2), 136.87 (C-6), 108.61 (C-5), 90.03 (C-1'), 89.22 (C-4'), 88.74 (C-2'), 74.72 (C-3'), 60.83 (C-5').

ESI-HRMS m/z: calculated for C$_9$H$_{10}$N$_2$NaO$_5$ 249.0482. found 249.0487.

Formation of the Sidechain:

2-mercaptoethanol (1.17 g, 15 mmol) was added dropwise to a DCM/DIPEA (5/1, 10 mL) solution containing 2-DSP (5.0 g, 23 mmol). After 16 hours, the solvents were evaporated under vacuum and the slurry was taken up in ACN (25 mL). Imidazole (6.1 g, 60 mmol) and TBDMSCI (4.5 g, 30 mmol) were added and the reaction mixture was stirred at room temperature for 16 hours. Afterwards, the mixture was concentrated and column chromatographed with PE/MTBE (10/1) to obtain the title compound as a colorless oil (two-step yield: 77.5%).

Rf 0.29 (10:1 PE/MTBE)

¹H NMR (200 MHz, CDCl$_3$): δ 8.47-8.44 (m, 6'-H, 1H), 8.45 (dd, J=8, 2 Hz, 4'-H, 1H), 7.68-7.59 (m, 3'-H, 1H), 7.10-7.04 (m, 5'-H, 1H), 3.85 (t, J=6 Hz, H-1, 1H), 2.92 (t, J=6 Hz, H-2, 1H), 0.89 (s, tertBu-CH$_3$, 9H), 0.05 (s, Si—CH$_3$, 6H).

¹³C NMR (50 MHz, CDCl$_3$): δ 160.68 (C-2'), 149.68 (C-6'), 137.12 (C-4'), 120.66 (C-5'), 119.73 (C-3'), 61.50 (C-1), 41.65 (C-2), 26.00 (tertBu-CH$_3$), 18.44 (tertBu-C), −5.15 (Si—CH$_3$).

Conjugation:

Desiccated 2,2'-anhydrouridine (6.6 mmol, 1.5 g) was dissolved in dry DMA (10 mL). BF3.OEt$_2$ (10 mmol, 1.2 mL) was added and the solution was stirred at room temperature. After 5 minutes, the activated/protected side chain 1 (2 eq.) was added and the reaction was heated at 100° C. for 10 hours. The reaction mixture was dropped to a saturated sodium bicarbonate solution (100 mL) followed by extraction with ethyl acetate (3×100 mL). The organic phase was then washed with brine and dried over sodium sulfate and concentrated in vacuo.

The residue was column purified with DCM/MeOH (10/1) to obtain the target compound as a colorless oil (yield: 50%).

R$_f$ 0.33 (10:1 DCM/MeOH)

ESI-HRMS m/z: calculated for C$_{16}$H$_{19}$N$_3$O$_6$S$_2$ 414.0788. found 414.0794.

Protection of the 5' position of the ribose of the 2-oxo-pyrimidine nucleoside:

4,4'-Dimethoxytrityl chloride (0.12 g, 0.35 mmol) was added to a solution of the precursor compound (0.10 g, 0.24 mmol) in 2 mL of anhydrous pyridine. The reaction mixture was stirred for 16 hours at room temperature and the reaction was monitored via thin-layer chromatography.

After quenching the reaction for 0.5 hours in the presence of 0.5 mL of methanol, the solvents were removed under vacuum and the residue was redissolved in ethyl acetate, washed with water, saturated sodium bicarbonate solution, brine and dried over sodium sulfate. The organic phase was then concentrated and the resulting yellow foam was column chromatographed using a gradient of 0-5% triethylamine in dichloromethane to give the title compound (63%) as a pale yellow foam.

Rf 0.19 (20/1 DCM/triethylamine)

ESI-HRMS m/z: calculated for C$_{37}$H$_{38}$N$_3$O$_8$S$_2$ 716.2095. found 716.2098.

Biological Assays

In Vitro Target Downregulation

Conjugates were applied at logarithmically increasing concentrations starting from 0.1 nM. The Bcl-2 expression levels are expressed as percent of Bcl-2 level in untreated cells and have been corrected for Actin (internal loading control). To assess the unassisted cellular uptake, protein levels were compared with Bcl-2 expression of the cells treated with the naked oligonucleotide of the same sequence. As an additional control and in order to observe the possible effect of complexation with the same peptide sequence, cells were subjected to a mixture of the corresponding oligonucleotide and oligopeptide precomplexed at equal concentrations.

Conjugate with L-Lysine Residues

Figure 5:
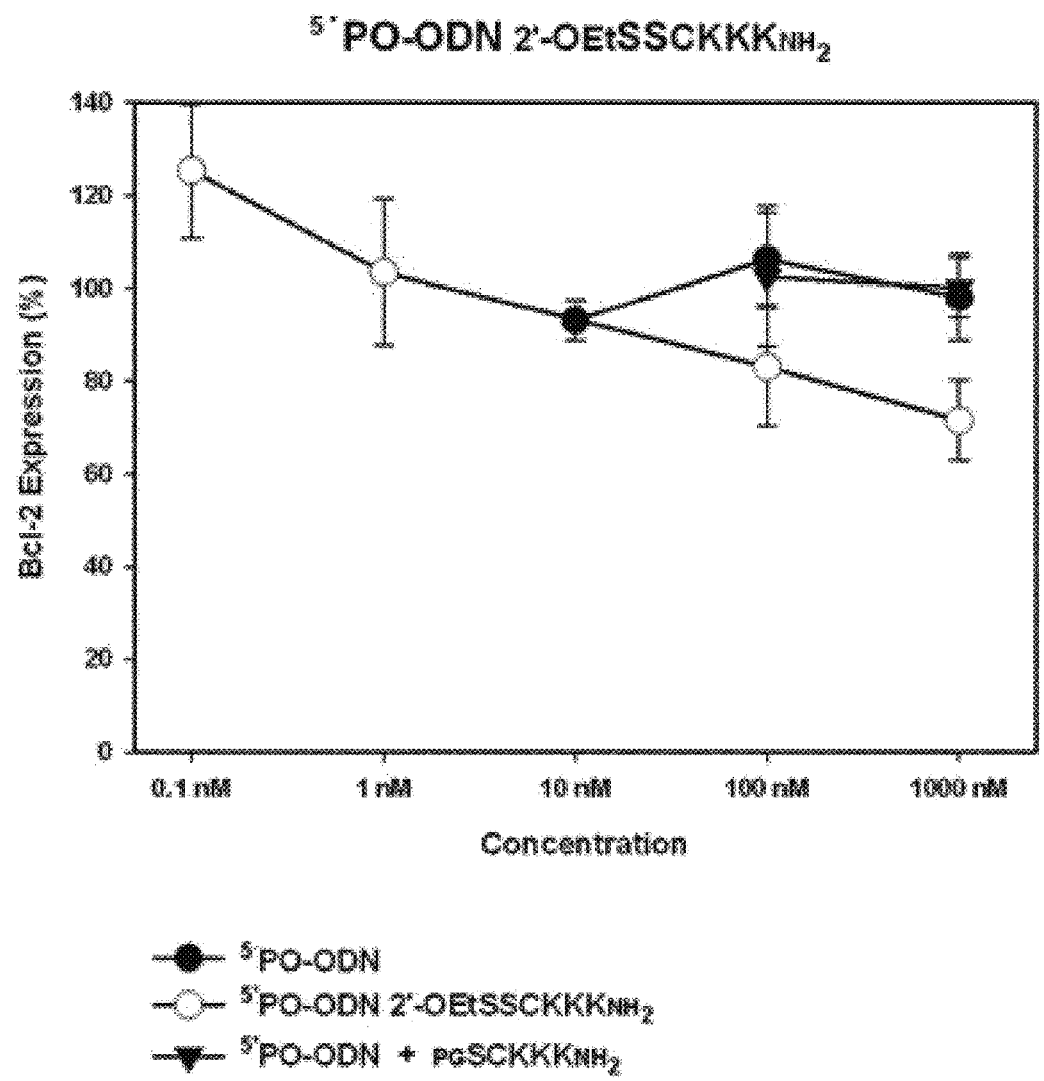
FIG. 5 shows a Bcl-2 Western blot analysis of 5'-PO-ODN2'-OET-S—S—C—KKK—NH$_2$ in 607B cell line. Vertical bars represent standard deviation of 3-6 determinations.

As conjugate having a L-cysteine and 3 L-lysine residues 5'-PO-ODN2'-OET-S—S—C—KKK—NH$_2$ was tested. There was no significant Bcl-2 downregulation at lower concentrations as can be seen in FIG. 5. The inhibitory effect was however determined to be statistically significant at 1000 nM (p=0.023). Compared with the naked oligonucleotide, the oligonucleotide pre-complexed with H-Cys-(SO$_3$H)-Lys-Lys-Lys-NH$_2$ did not show any significant downregulation at the last two concentrations tested. The Bcl-2 downregulation produced by the conjugate was significant compared with the oligolysine-oligonucleotide complex (p=0.010).

Figure 6:
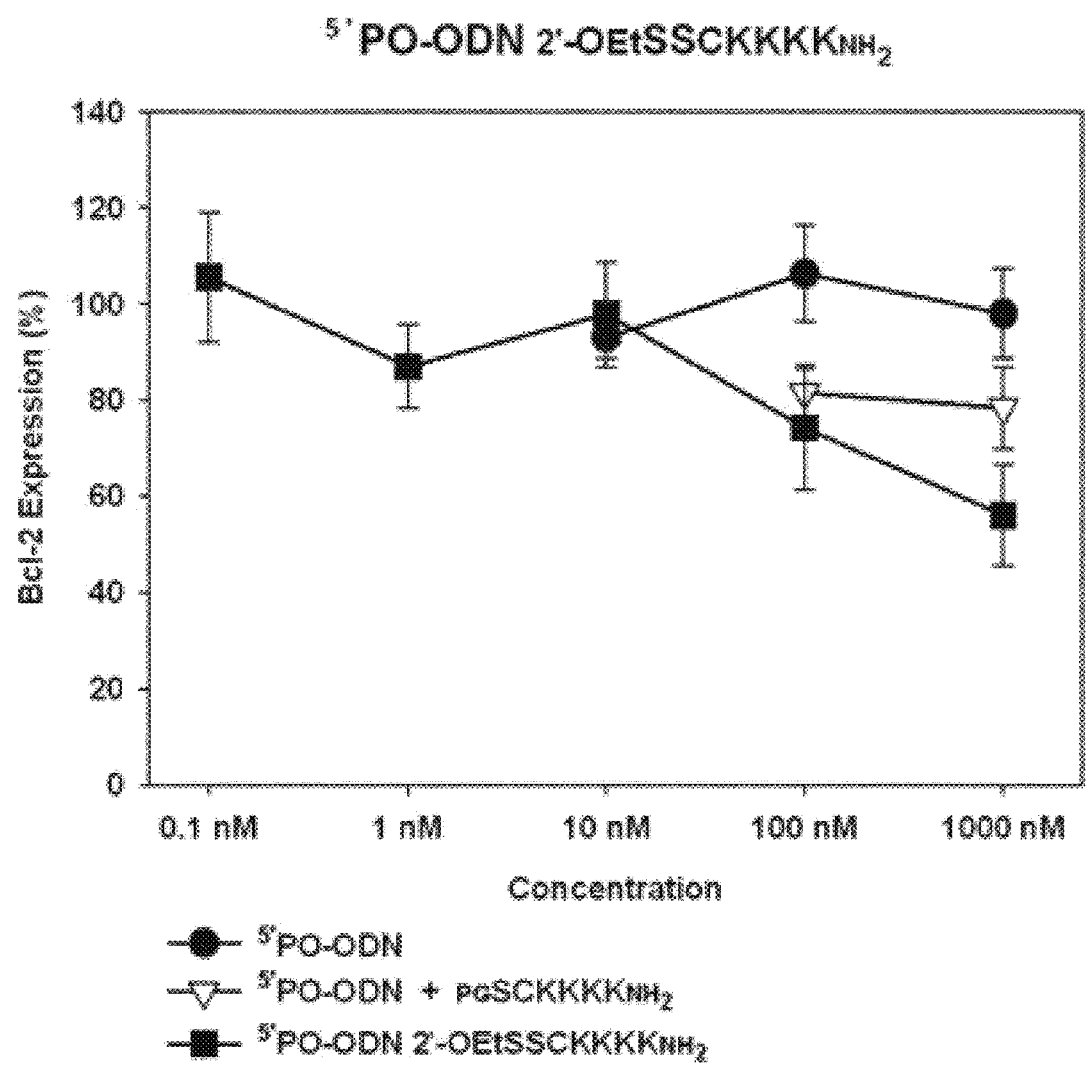
FIG. 6 shows a Bcl-2 Western blot analysis of 5'-PO-ODN2'-OET-S—S—C—KKKK—NH$_2$ in 607B cell line. Vertical bars represent standard deviation of 3 to 6 determinations.

As conjugate having a L-cysteine and 4 L-lysine residues 5'-PO-ODN2'-OET-S—S—C—KKKK—NH$_2$ was tested in FIG. 6. The oligonucleotide covalently conjugated to H-Cys (SO$_3$H)-Lys-Lys-Lys-Lys-NH$_2$ caused statistically significant downregulation of the Bcl-2 at the last two concentrations (100 nM, p=0.028; 1000 nM, p=0.007). However, complexation of the oligonucleotide with the corresponding oligopeptide only at 1000 nM resulted in a significant decrease (p=0.045) in the Bcl-2 expression level as shown in FIG. 6. However, a significant difference (p=0.045) could be observed between the downregulatory effect of the conjugate (1.75-fold) compared with the effect of the complex (1.25-fold).

Figure 7:
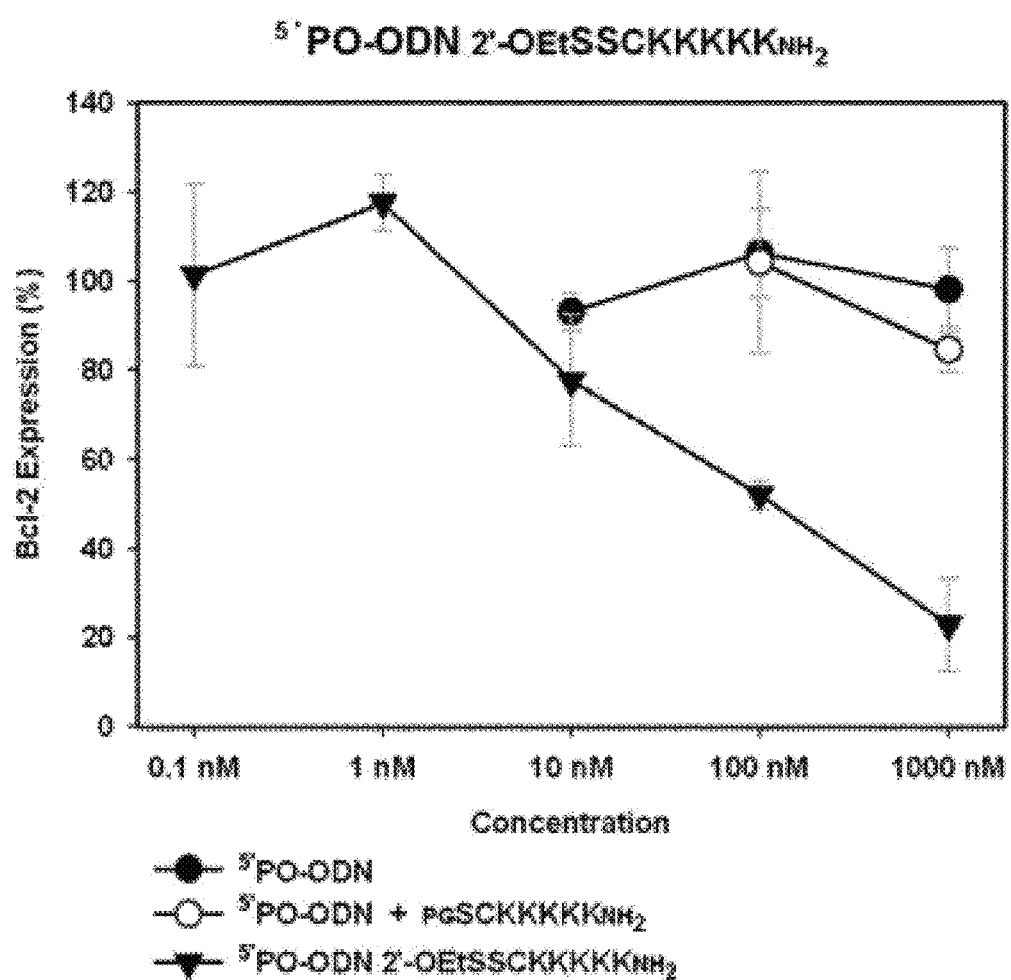
FIG. 7 shows a Bcl-2 Western blot analysis of 5'-PO-ODN2'-OET-S—S—C—KKKKK—NH$_2$ in 607B cell line. Vertical bars represent standard deviation of 3 to 6 determinations.

As conjugate having a L-cysteine and 5 L-lysine residues 5'-PO-ODN2'-OET-S—S—C—KKKKK—NH$_2$ was tested in FIG. 7.

Conjugates with H-Cys(SO$_3$H)-Lys-Lys-Lys-Lys-Lys-NH$_2$ suppressed Bcl-2 expression at 100 nM (p<0.001) and 1000 nM (p<0.001) significantly as shown in FIG. 7. Oligonucleotide in complex with the same oligopeptide produced no significant inhibition in this concentration range. The difference between the inhibitory effect of the conjugate and the complex was at both concentrations (100 nM, p=0.012; 1000 nM, p<0.001) significant.

Figure 8:
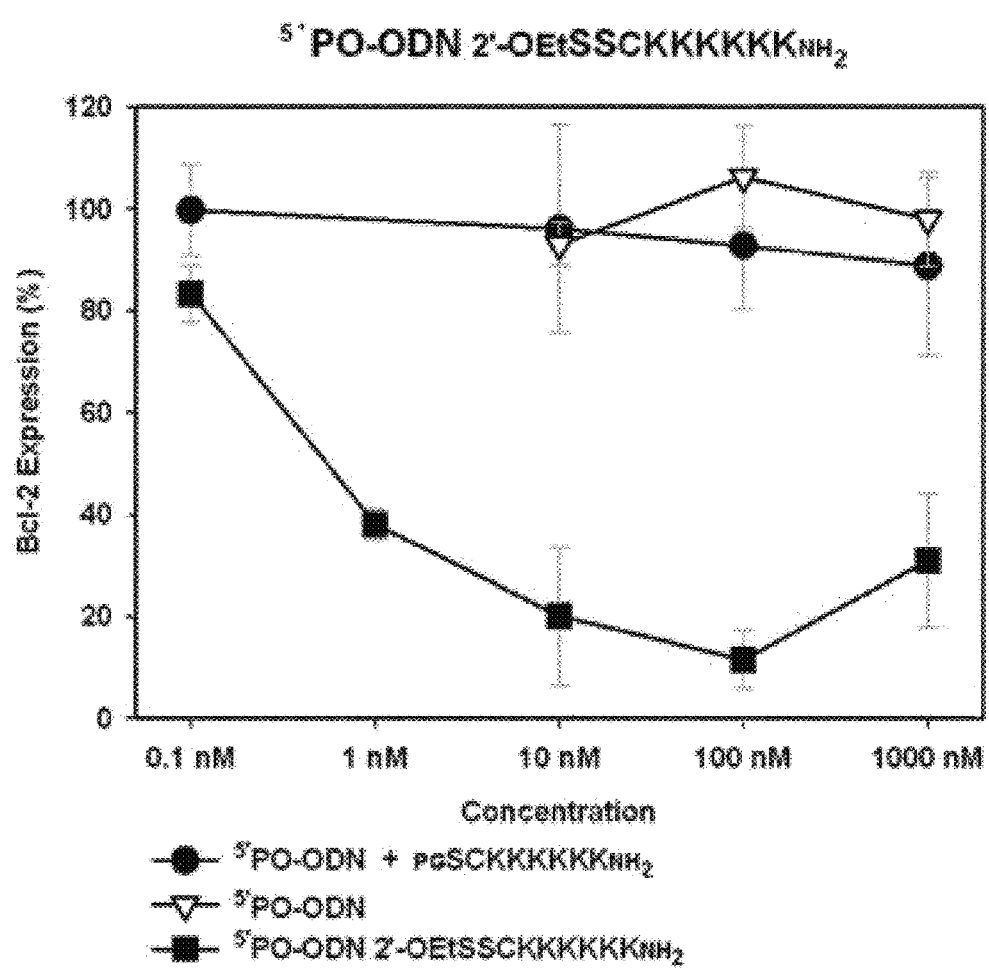
FIG. 8 shows a Bcl-2 Western blot analysis of 5'-PO-ODN2'-OET-S—S—C—KKKKKK—NH$_2$ in 607B cell line. Vertical bars represent standard deviation of 3 to 6 determinations.
Figure 13:
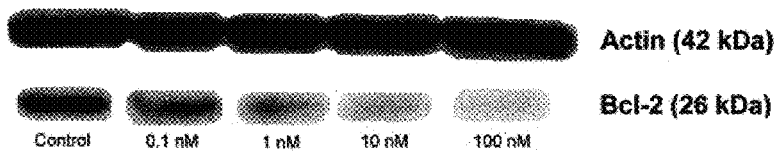
FIG. 13 shows a representative western blot analysis of cell lysates after treatment with 5'-PO-ODN2'-OET-S—S—C—KKKKKK—NH₂ at the indicated concentrations.

As conjugate having a L-cysteine and 6 L-lysine residues 5'-PO-ODN2'-OET-S—S—C—KKKKKK—NH$_2$ was tested in FIG. 8. Conjugate of the oligonucleotide with H-Cys(SO$_3$H)-Lys-Lys-Lys-Lys-Lys-Lys-NH$_2$ demonstrated the highest potency in the same concentration range tested. Here, even at 10 nM concentration a significant downregulation of the Bcl-2 expression was noted (p<0.001). The inhibitory effect increased dose-dependently (SDS-PAGE analysis see FIG. 13), culminated at 100 nM concentration in a 9-fold suppression of Bcl-2 but appeared to be leveling off at 1000 nM concentration.

The inhibitory effect of the complex formed of the isosequential oligonucleotide with the same oligopeptide at equal concentrations was shown to be not statistically significant. A comparison between the effects of the conjugate and the complex showed significant differences at the last four concentrations tested (1 nM, 10 nM, 100 nM and 1000 nM, all p values smaller than 0.001).

Conjugate with PEG-Chain

Figure 9:
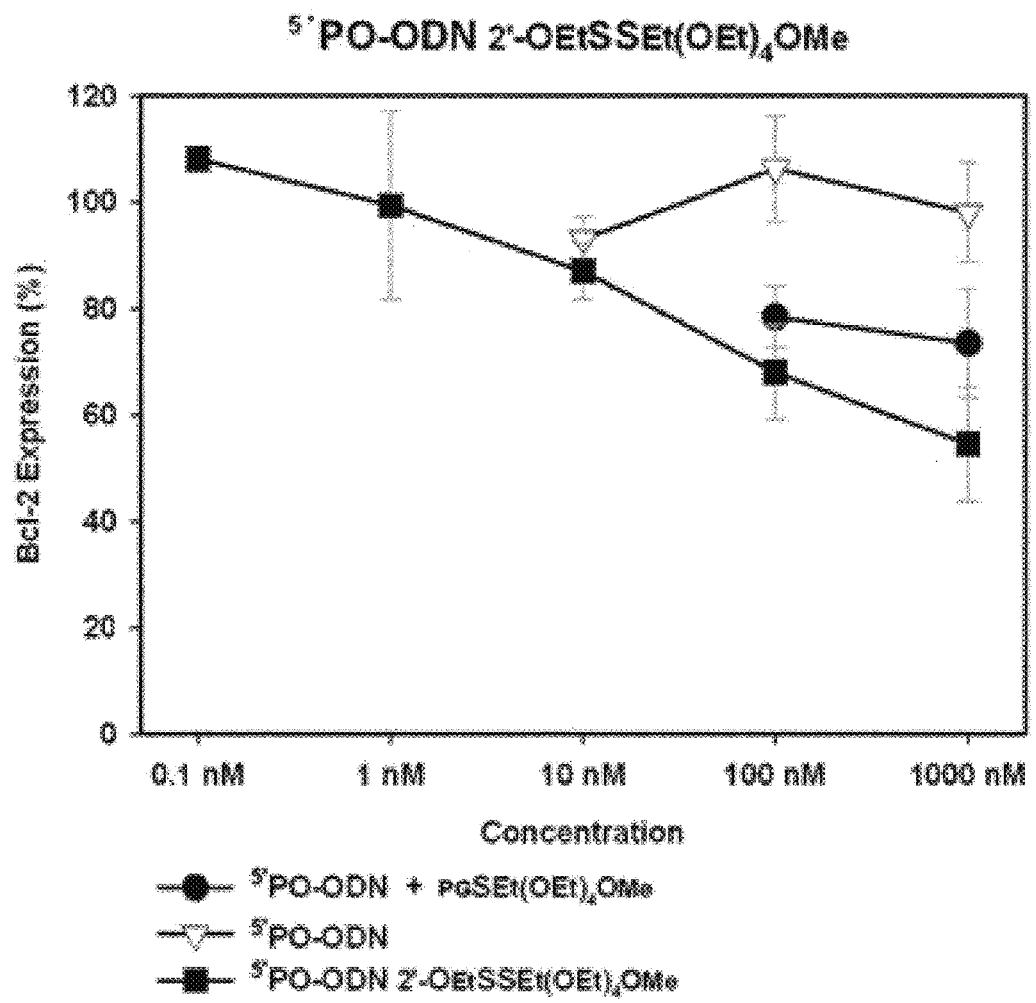
FIG. 9 shows a Bcl-2 Western blot analysis of 5'-PO-ODN2'-OET-S—S-Et(OEt)$_4$-OMe in 607B cell line. Vertical bars represent standard deviation of 3 to 6 determinations.

As conjugate having a $PEG_5$-chain 5'-PO-ODN2'-OET-S—S-Et(OEt)$_4$-OMe was tested in FIG. 9. Coupling of the $PEG_5$ that corresponds to Et(OEt)$_4$-OMe with the oligonucleotide resulted in a statistically significant effect on Bcl-2 expression (FIG. 9) at 100 nM (p=0.001) and 1000 nM (p<0.001) concentrations. The difference between the down-regulatory effect of the conjugate and the mixture of the isosequential oligonucleotide with the same concentration of $PEG_5$ was not enough to conclude an exclusive effect for conjugation.

Our data demonstrate the feasibility of conjugation of oligonucleotide with oligolysines, particularly with 5 and 6 lysine residues and $PEG_5$ through a cleavable disulfide linker for improving the efficacy of the oligonucleotide in cell culture studies. However in the case of the $PEG_5$ conjugate, at least in the concentration range tested, the improved efficacy is not necessarily perceived to be a consequence of conjugation.

Cell Proliferation/Viability Assay

Quantifying cell viability is crucial for understanding cancer biology, compound toxicity and cellular response to cytokines and other biological questions. A number of methods have been developed to study cell viability and proliferation in cell populations. Metabolic activity assays usually measure mitochondrial activity. A microtiter plate assay using the tetrazolium salt MTT is now widely used to quantitate cell proliferation and cytotoxicity. As tetrazolium salts are reduced to a colored formazan (by the "succinatetetrazolium reductase" system) only by metabolically-active cells, these assays detect exclusively viable cells.

Figure 10:
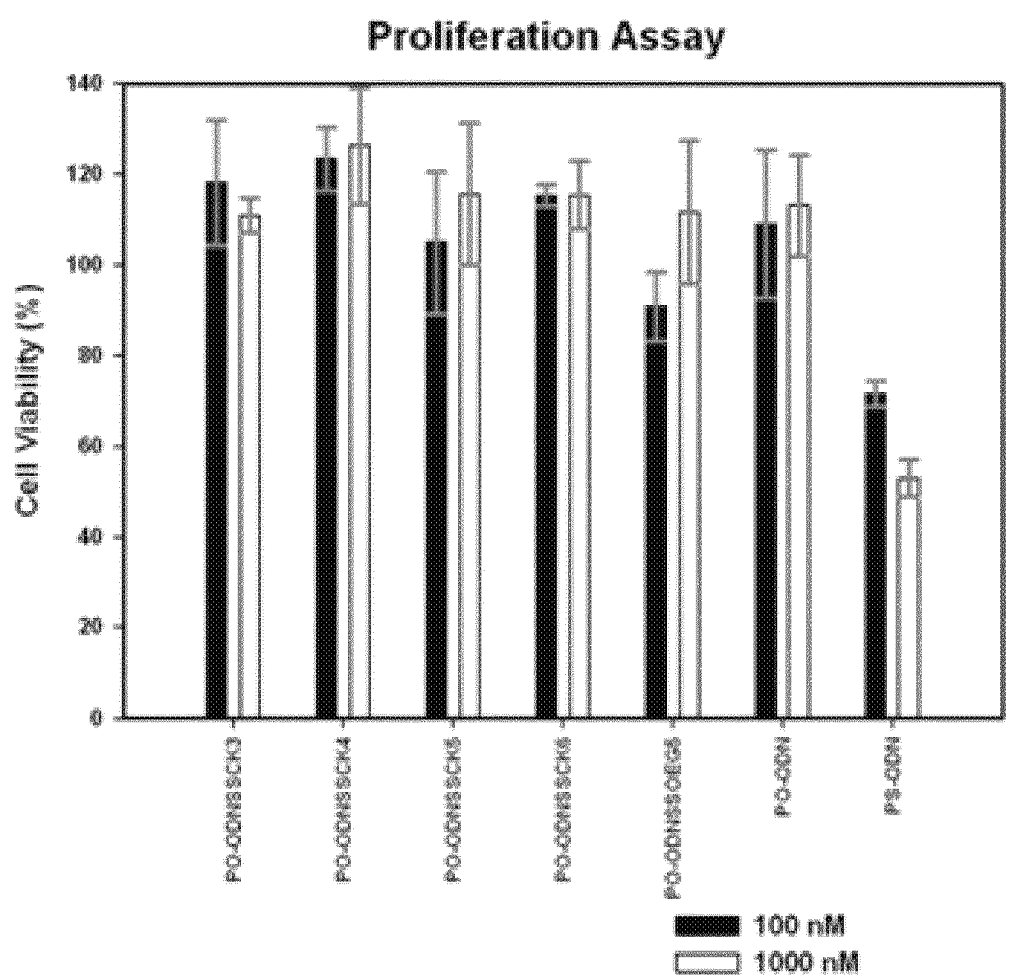
FIG. 10 shows a proliferation assay/cell viability assay of the conjugates without use of a transfection agent. Vertical bars represent standard deviation of triplicate determinations.

In FIG. 10 a cell viability assay of the conjugates without use of a transfection agent is shown. Further, the intrinsic apoptotic effect of the phosphorothioate can be seen. The vertical bars represent standard deviation of triplicate determinations.

The cell viability has been expressed as percentage of untreated cells. No significant differences were observed for the phosphodiester conjugates compared with untreated cells. Based on our data, it is to be concluded that the conjugates do not have any toxic effects on 607B cell line. However, the unmodified phosphorothioate oligonucleotide showed an intrinsic apoptotic effect as can be seen in FIG. 10 at both concentrations tested (% cell viability at 100 nM: 71.5%±2.9 and 52.9%±4.1 at 1000 nM).

Apoptosis Assay

Although the conventional cytotoxicity assays may be suitable for detecting the later stages of apoptosis, other assays were needed to detect the early events of apoptosis, researchers discovered that proteases, referred to as caspases, were involved in the early stages of apoptosis.

Ac-DEVD-AMC is a synthetic tetrapeptide fluorogenic substrate for Caspase-3 (CPP32) and contains the amino acid sequence of the PARP cleavage site. The tetrapeptide substrate can be used to identify and quantify the Caspase-3 activity in apoptotic cells. Caspase-3 cleaves the tetrapeptide between D and AMC, thus releasing the fluorogenic AMC, which can be quantified in a spectrofluorometer.

Figure 11:
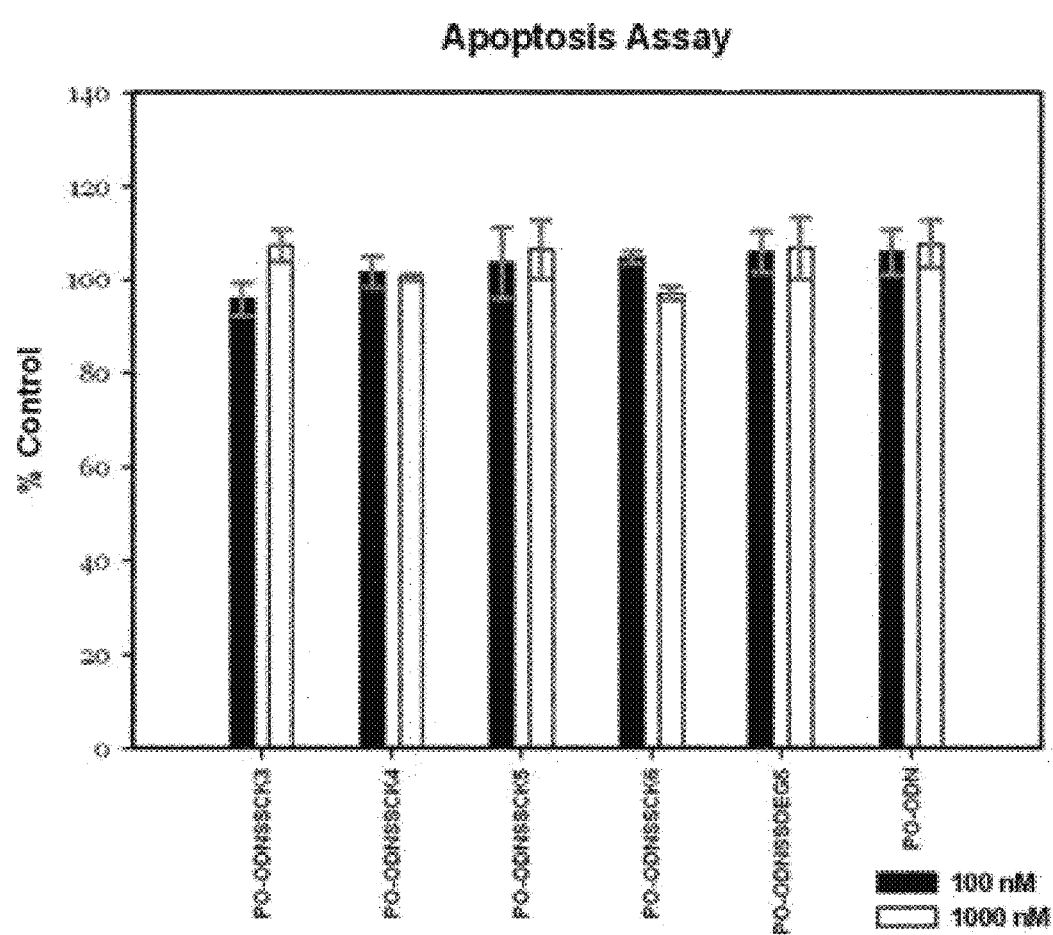
FIG. 11 shows an apoptosis assay of the oligonucleotide conjugates without use of a transfection agent. Vertical bars represent standard deviation of triplicate determinations.

In FIG. 11, an apoptosis assay of the oligonucleotide conjugates without use of a transfection agent is shown. Vertical bars represent standard deviation of triplicate determinations. The results show no significant caspase activation, and thus confirm the absence of toxicity.

Based on the foregoing analyses and in order to confirm the observed inhibitory effect and to assess the therapeutic potential of the conjugates, additionally tests were performed as far as the chemosensitizing effect of the selected conjugates in combination with a representative antineoplastic agent, i.e. cisplatin are concerned.

Chemosensitization Test

Metastatic melanoma is inherently resistant to most systemic treatments. Cytotoxic chemotherapy triggers cancer cell death by activating an apoptotic cascade that is initiated by mitochondrial release of cytochrome C and activation of caspase 9. Drug resistance in melanoma has been partially attributed to overexpression of Bcl-2, an anti-apoptotic protein that blocks the release of cytochrome C. Overexpression of Bcl-2 probably occurs in more than half of all cancers, and in addition to regulating cell death triggered by developmental and physiologic cues, it renders tumor cells resistant to apoptosis induced by cytotoxic stress conditions. Notably, melanoma metastases of patients not responding to chemotherapy have been reported to express particularly high levels of Bcl-2 protein, supporting the concept of Bcl-2 as a key regulator for chemotherapy-triggered apoptosis in malignant melanoma.

Generally, ASONs targeting apoptosis-regulating proteins such as clusterin, survivin or Bcl-2 proteins are used in combination with antiproliferative drugs. The rationale for such a strategy is that cancer cells respond to the stress of chemotherapeutic agents by increasing the production of pro-survival proteins. Co-administration of ASONs with anticancer drugs (antiproliferative drugs) like Dacarbazine, Cisplatin, Paclitaxel has been demonstrated to reduce the required doses of the ASON and/or anticancer agent to eradicate tumour cells (studies with OGX-427 and ISIS 3521).

The use of specific inhibitors of key cellular functions, in combination with so-called "dirty" conventional drugs with a myriad of mechanisms of action, might be the route to take in our quest for improving treatment outcome. Cisplatin is an important antineoplastic drug used against a variety of solid tumors. Ototoxicity is a dose-limiting side effect of cisplatin treatment. Sensorineural hearing loss is a common clinical problem at high dose.

Having demonstrated that the conjugates according to the invention are capable of suppressing Bcl-2 levels, the hypothesis was tested whether such an effect might chemosensitize human melanoma cell line towards anti-neoplatic agents. Thus, a dose-ranging experiment was performed with logarithmic cisplatin concentrations starting from 0.01 μM to 100 μM. Accordingly, the cells were treated with the conjugates at 100 nM (the optimal concentration based on the Western blotting analyses) for 24 hours before being subjected to cisplatin concentrations for another 24 hours. The cell viability was then determined as percent of control (untreated cells) and was compared with cisplatin-only treatment.

Figure 12:
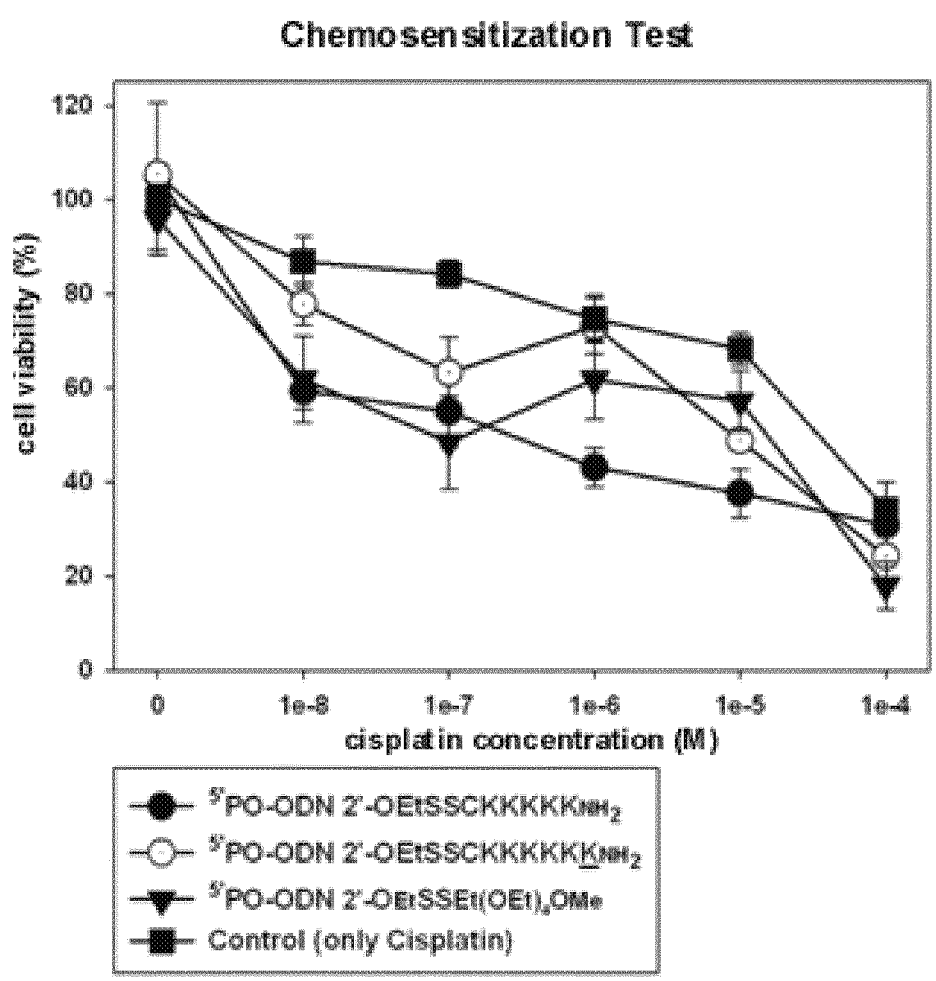
FIG. 12 shows the chemosensitizing effect of conjugates (100 nM) in combination with cisplatin in 607B cells. The naked phosphodiester oligonucleotide did not show any significant effect in this concentration range. Vertical bars represent standard deviation of 3 to 6 determinations.

Conjugates applied at 100 nM markedly facilitated the induction of apoptosis particularly at lower cisplatin concentrations (see also FIG. 11 and FIG. 12).

5'PO-ODN2'-OEt-S—S—C—KKKKK—NH$_2$ (the conjugate with a cysteine and 5 lysine residues) showed however a significant chemosensitizing effect (1.5- to 1.8-fold) over a wider range of cisplatin concentrations (0.01 μM, 0.1 μM, 1 μM and 10 μM; p≤0.003).

5'PO-ODN2'-OEt-S—S—C—KKKKKK—NH$_2$ (the conjugate with a cysteine and 6 lysine residues) lowered the apoptotic threshold at 0.1 μM (p=0.011) and 10 μM (p<0.011), 1.3-fold and 1.4-fold, respectively.

5'PO-ODN2'-OEt-S—S-Et(OEt)$_4$-OMe (the conjugate with the PEGS chain, i.e. the Et(OEt)$_4$-OMe) enhanced apoptosis 1.4-fold at the lowest concentration of cisplatin (0.01 μM) and 1.7-fold at 0.1 μM.

In FIG. 12 the chemosensitizing effect of conjugates (100 nM) in combination with cisplatin in 607B cells is shown. The naked phosphodiester oligonucleotide did not show any significant effect in this concentration range. Vertical bars represent standard deviation of 3-6 determinations. In view of the results of the chemosensitization test, it could be shown that the conjugates and oligonucleotides according to the invention could enhance the apoptotic effect of cisplatin (see FIG. 12, concentrations $10^{-8}$ and $10^{-7}$) particularly at lower concentrations (reduced risk of adverse/toxic effects) without inducing apoptosis (see FIG. 10 and FIG. 12). In this sense and in light of the so-called intrinsic non-specific apoptotic effect associated with use of phosphorothioates, it can be concluded that these conjugates and oligonucleotides pose more compelling characteristics as potential therapeutic candidates with a broader therapeutic index. The conjugates and oligonucleotides according to the invention demonstrated in the absence of uptake-enhancing agents, high efficacy in downregulating the target protein (Bcl-2) as well as sensitizing the cells, in particular 607B melanoma cells, towards the effect of antiproliferative drugs, e.g cisplatin. Their efficacy with concomitant lack of intrinsic nonspecific apoptotic effect observed for phosphorothioates enables them to be employed in downregulation of a wide variety of target proteins.

polymers with basic charges at neutral or acidic pH or lipid acids or tocopherol;

Y represents a spacer, wherein the spacer Y represents a —(CH$_2$)$_m$—NH$_2$—CO— group, wherein m is an integer of 1 to 6 or represents an alkyl group having 1 to 6 carbon atoms; and n is an integer ranging from 1 to the oligonucleotide length of P.

2. The conjugate according to claim 1, wherein the natural, artificial and/or modified oligonucleotide P comprises natural, artificial and/or modified nucleosides having natural, artificial and/or modified nucleobases, wherein a number of said nucleosides form an oligonucleotide selected from the group consisting of:

phosphodiester oligonucleotide (PDOs), phosphorothioate oligonucleotides (PSOs), phosphorodiamidate morpholino oligonucleotides (PMOs), peptide nucleic acids (PNAs), locked nucleic acids (LNAs), ethyl bicyclic nucleic acids (cET BNA), 2'-fluor oligonucleotides, 2'-fluoro oligoarabinonucleotides and combinations thereof.

3. The conjugate according to claim 1, wherein the linker L is covalently linked via the oxygen atom to the 2' position of the ribose ring of a phosphodiester oligonucleotide, a phosphorothioate oligonucleotide, at the 2' position of the morpholine ring of a phosphorodiamidate morpholino oligonucleotide, or an equivalent position of a peptide nucleic acid.

The invention claimed is:

1. A conjugate of formula I,

P-(L-S—S—Y—X)$_n$    (I)

wherein

P represents a natural, artificial and/or modified oligonucleotide,

L represents a linker group attached to one or more nucleosides at the 2' position of one or more ribose rings of the oligonucleotide within the oligonucleotide sequence;

S represents sulfur;

X represents a ligand, wherein the ligand is selected from the group consisting of peptides of 1 to 40 amino acids, preferably peptides with more than 20% arginine or lysine amino acids or natural basic peptides such as protamine, peptides for cellular uptake or intracellular transport, polyethylene glycols of preferably 2 to 200 ethylene glycol units, and 4. The conjugate according to claim 1, wherein the linker L represents a linear alkyl linker of 1 to 10 carbon atoms, or a polyethylene glycol linker of 1 to 20 ethylene glycol units.

5. The conjugate according to claim 1, wherein the ligand X is selected from the group consisting of peptides of 1 to 40 amino acids, preferably peptides with more than 50% arginine or lysine amino acids, and natural basic peptides such as protamine; polyethylene glycols of preferably 2 to 50 ethylene glycol units, preferably a polyethylene glycol having 1 to 20 ethylene glycol units; polymers with basic charges at neutral or acidic pH, comprising polyamines, linear and branched polyethylene imines, lipid acids and tocopherol.

6. The conjugate according to claim 1, wherein the linker L represents a C$_2$ to C$_{10}$ alkyl linker, the ligand X represents polylysine or polyethylene glycol and the spacer Y represents a —(CH$_2$)$_m$—NH$_2$—CO— group.

7. The conjugate according to claim 1, wherein the linker L represents a polyethylene glycol linker of 1 to 20 ethylene glycol units, the ligand X represents a ligand for receptor-specific interactions and the spacer Y represents an ethyl group.

8. The conjugate according to claim 1, wherein the conjugate comprises one or more additional linkers L', one or more additional ligands X' and one or more additional spacers Y' at the 2'-O—, 3'-O—, and 5'-O-positions of the oligonucleotide.

9. The conjugate according to claim 7, wherein the additional linker L' is selected from the group consisting of linear alkyl linkers of 1 to 10 carbon atoms, and polyethylene glycol linkers of 1 to 20 ethylene glycol units, the additional ligand X' of the conjugate is a dye, a fluorescence dye, a fluorescence marker or being a ligand X and the additional spacer Y' is a —$(CH_2)_m$—$NH_2$—CO— group, wherein m is an integer of 1 to 6 or represents an alkyl group having 1 to 6 carbon atoms or an alkyl group having 1 to 6 carbon atoms.

10. A pharmaceutical composition comprising the conjugate according to claim 1 and optionally pharmaceutically acceptable excipients, carriers or diluents.

11. A pharmaceutical kit comprising (i) the conjugate according to claim 1 and (ii) an antiproliferative drug.

12. The conjugate according to claim 1 for use as a medicament or a tool in biomedical research.

13. The conjugate according to claim 1 for the treatment of a disease or disorder that can be at least in part alleviated by therapy.

14. The conjugate of claim 13, wherein the disease or disorder is selected from the group consisting of bacterial infections, viral infections, cancer, metabolic diseases and immunological disorders, and is preferably cancer.

15. A pharmaceutical kit comprising (i) the pharmaceutical composition according to claim 10 and (ii) an antiproliferative drug.

* * * * *

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct; complementary to human
      bcl-2 mRNA

<400> SEQUENCE: 1
ttctcccagc gtgcgcca                                                   18
```